US010779833B2

(12) United States Patent
Williams

(10) Patent No.: US 10,779,833 B2
(45) Date of Patent: *Sep. 22, 2020

(54) ANVIL ASSEMBLY DELIVERY SYSTEM

(71) Applicant: Covidien LP, Mansfield, MA (US)

(72) Inventor: Justin Williams, Southbury, CT (US)

(73) Assignee: Covidien LP, Mansfield, MA (US)

(*) Notice: Subject to any disclaimer, the term of this patent is extended or adjusted under 35 U.S.C. 154(b) by 286 days.

This patent is subject to a terminal disclaimer.

(21) Appl. No.: 15/859,898

(22) Filed: Jan. 2, 2018

(65) Prior Publication Data

US 2018/0116668 A1    May 3, 2018

Related U.S. Application Data

(63) Continuation of application No. 14/564,571, filed on Dec. 9, 2014, now Pat. No. 9,855,045.

(51) Int. Cl.
| | | |
|---|---|---|
| *A61B 17/115* | (2006.01) | |
| *A61B 17/04* | (2006.01) | |
| *A61B 17/072* | (2006.01) | |
| *A61B 17/00* | (2006.01) | |
| *A61B 90/00* | (2016.01) | |

(52) U.S. Cl.
CPC ....... *A61B 17/1155* (2013.01); *A61B 17/0467* (2013.01); *A61B 17/0482* (2013.01); *A61B 90/06* (2016.02); *A61B 2017/00292* (2013.01); *A61B 2017/00473* (2013.01); *A61B 2017/07257* (2013.01); *A61B 2090/037* (2016.02); *A61B 2090/061* (2016.02); *A61B 2090/0807* (2016.02)

(58) Field of Classification Search
CPC ............. A61B 17/1114; A61B 17/115; A61B 17/1155; A61B 17/068; A61B 2017/072

USPC .......................................... 227/175.1–180.1
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |

(Continued)

FOREIGN PATENT DOCUMENTS

| | | | |
|---|---|---|---|
| CA | 908529 | A | 8/1972 |
| DE | 1057729 | B | 5/1959 |

(Continued)

OTHER PUBLICATIONS

Australian Office Action dated Aug. 9, 2019, issued in AU Appln. No. 2015252140.

(Continued)

*Primary Examiner* — Nathaniel C Chukwurah
(74) *Attorney, Agent, or Firm* — Carter, DeLuca & Farrell LLP

(57) ABSTRACT

An anvil assembly suitable for trans-oral delivery is provided. The anvil assembly includes a housing configured to receive a guide suture that is severed during a stapling procedure. An anvil delivery assembly including the anvil assembly and a suture guide assembly secured to the anvil assembly is also provided.

19 Claims, 21 Drawing Sheets

(56) References Cited

U.S. PATENT DOCUMENTS

| | | |
|---|---|---|
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |

(56) References Cited

U.S. PATENT DOCUMENTS

| | | |
|---|---|---|
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |

(56) References Cited

U.S. PATENT DOCUMENTS

| | | |
|---|---|---|
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 * | 2/2012 | Milliman ............ A61B 17/1114 227/175.1 |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,251 B2 | 4/2014 | Rebuffat et al. |
| 8,684,252 B2 | 4/2014 | Patel et al. |
| 8,733,611 B2 | 5/2014 | Milliman |
| 9,855,045 B2 * | 1/2018 | Williams ............ A61B 17/1155 |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |

(56) References Cited

U.S. PATENT DOCUMENTS

| | | |
|---|---|---|
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2042108 A2 | 4/2009 |
| EP | 2153781 A2 | 2/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 2001/054594 A1 | 8/2001 |
| WO | 2008/107918 A1 | 9/2008 |

OTHER PUBLICATIONS

Extended European Search Report dated Apr. 26, 2016, issued in European Application No. 15198366.5.

* cited by examiner

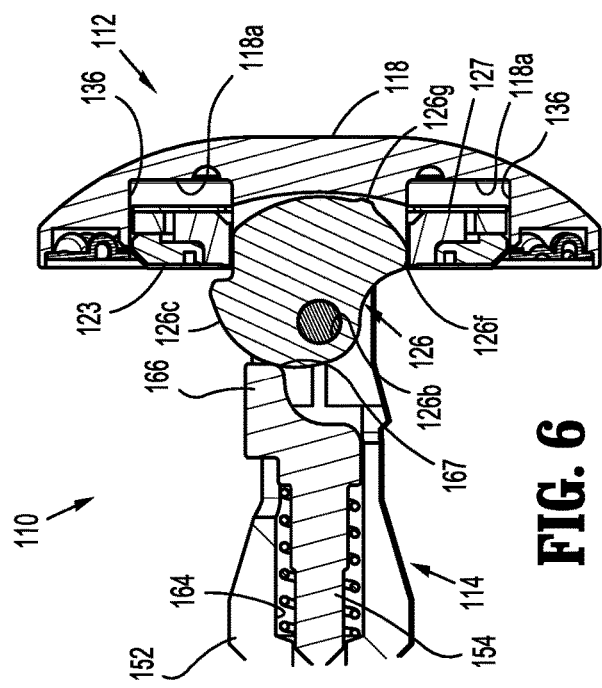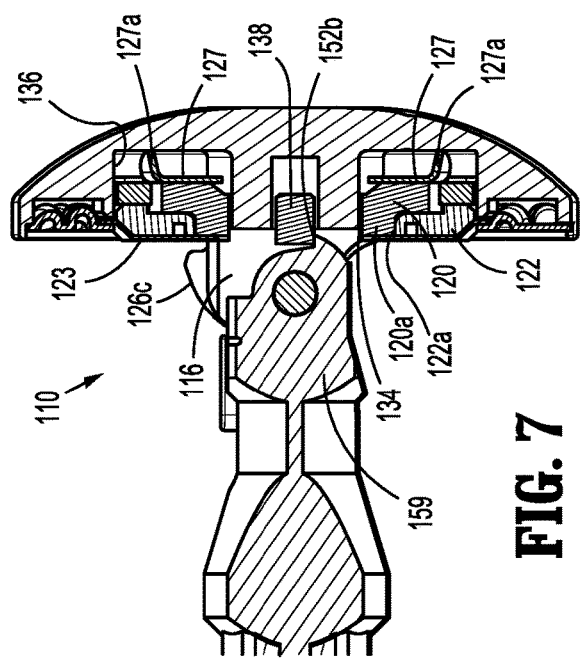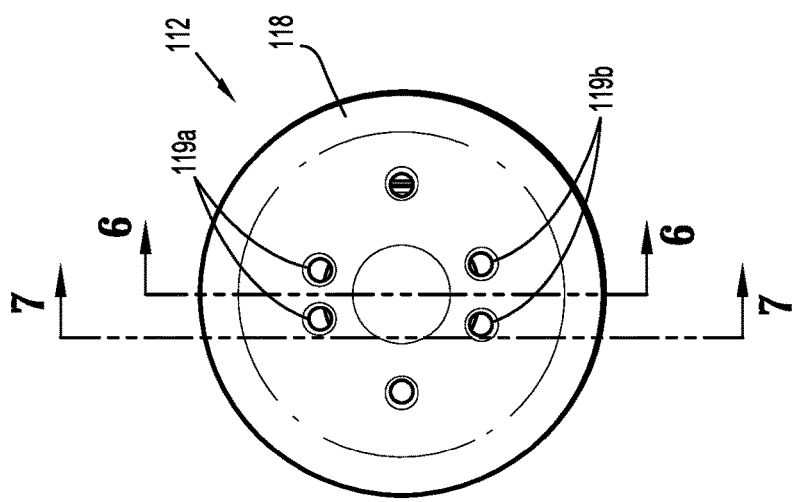

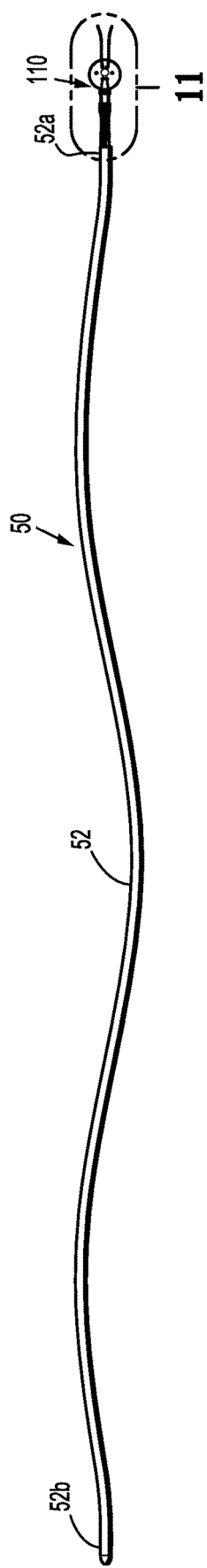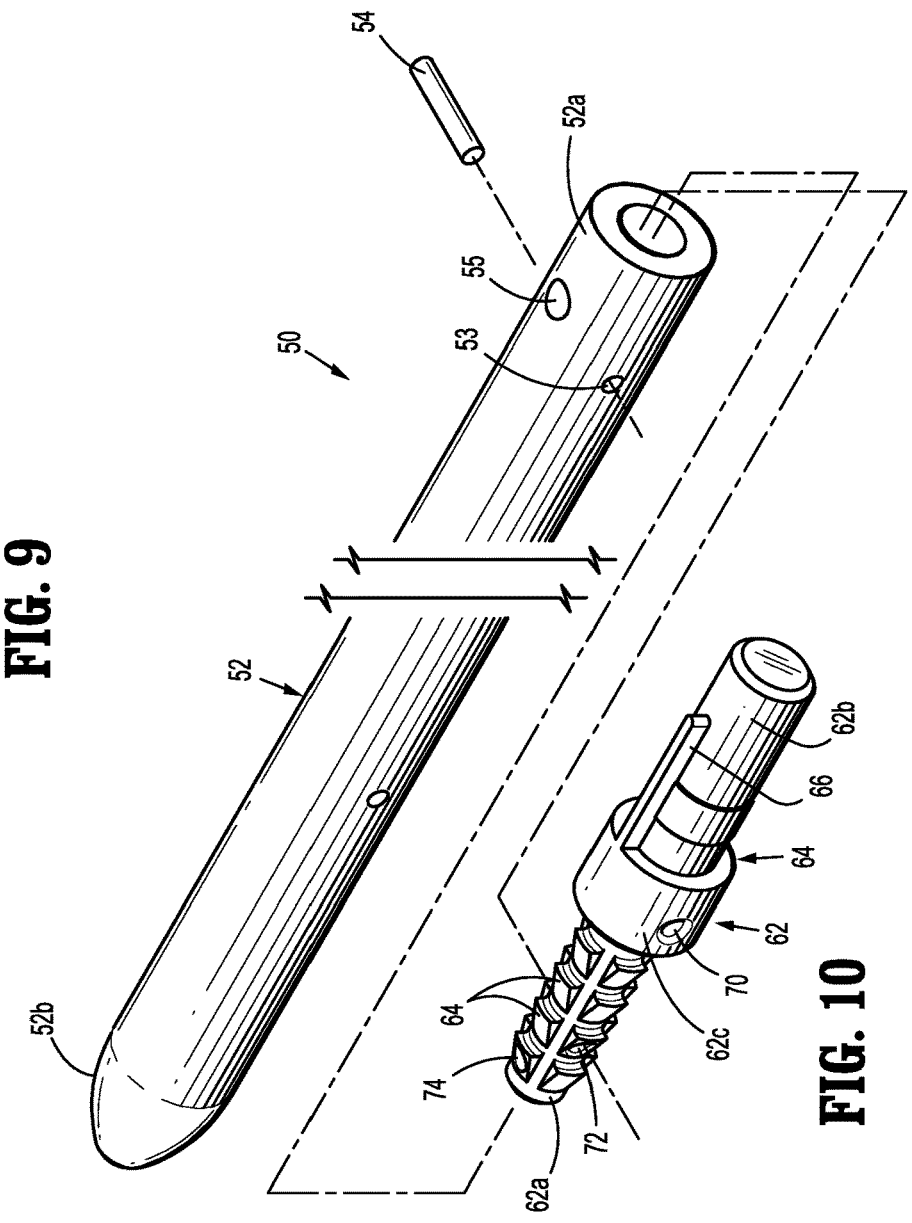
FIG. 9
FIG. 10

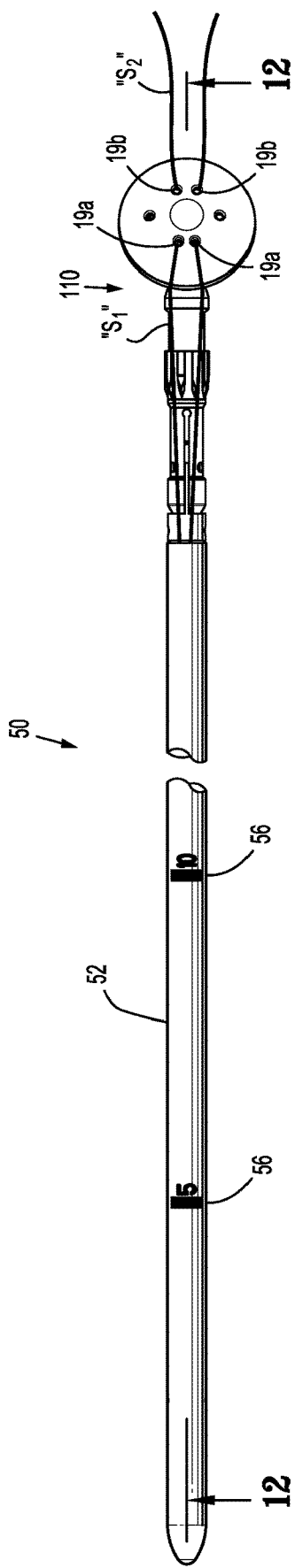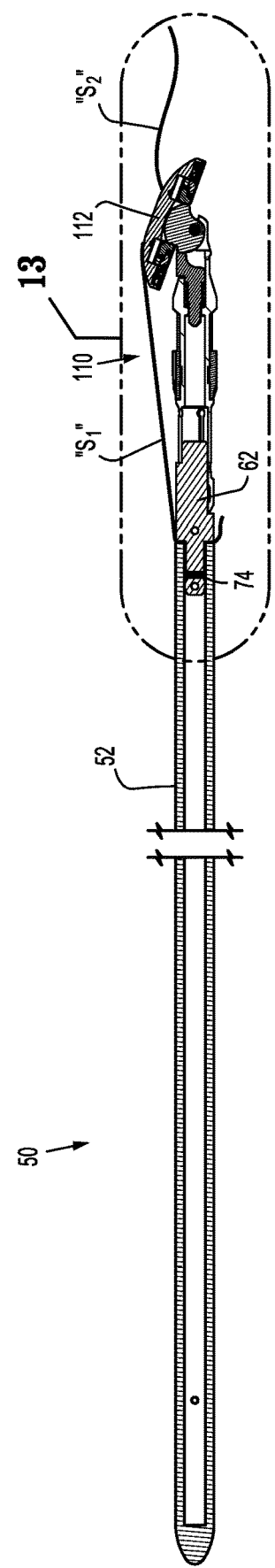

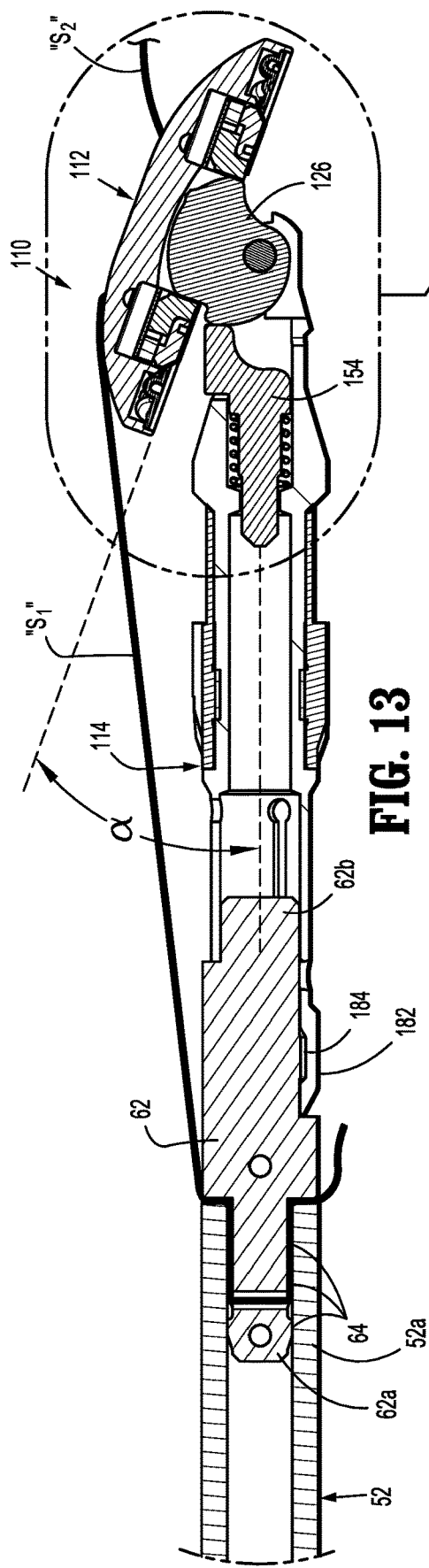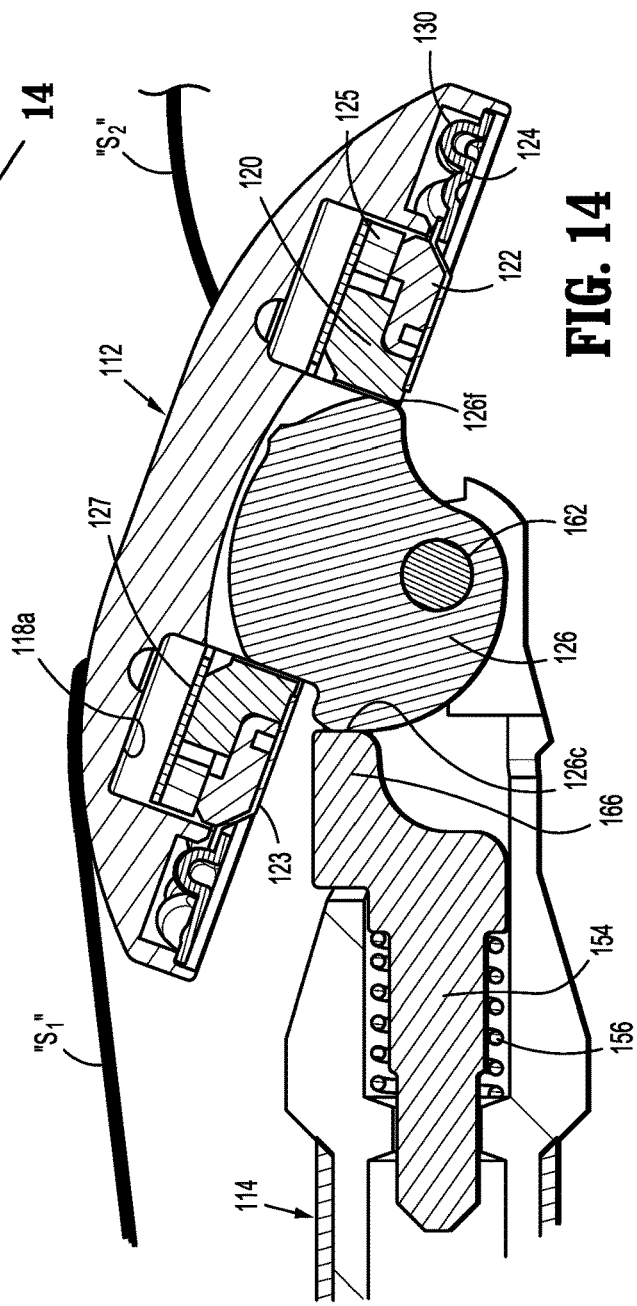

ANVIL ASSEMBLY DELIVERY SYSTEM

CROSS-REFERENCE TO RELATED APPLICATIONS

This application is a continuation of U.S. patent application Ser. No. 14/564,571 filed Dec. 9, 2014, now U.S. Pat. No. 9,855,045, and the disclosure of the above-identified application is hereby incorporated by reference in its entirety.

BACKGROUND

Technical Field

The present disclosure relates to an anvil assembly for use with a surgical stapling device. More particularly, the present disclosure relates to an anvil assembly for trans-oral delivery of the anvil assembly.

Background of Related Art

Trans-oral delivery systems for delivering an anvil assembly to a surgical site, e.g., the stomach, are known. In known delivery systems, a guide suture is threaded through one or more openings in the head of the anvil assembly to facilitate trans-oral insertion of the anvil assembly. The guide suture may be used to dislodge the anvil assembly if it becomes stuck within a body lumen during trans-oral delivery and/or to retrieve the anvil assembly in the event of an emergency, e.g., cardiac arrest. Improved methods for securing the guide suture to an anvil assembly to facilitate detachment of the guide suture from the anvil assembly once the anvil assembly is delivered to the surgical site and/or the stapling procedure has been performed is desirable.

SUMMARY

An anvil assembly for a surgical stapling device is provided. The anvil assembly includes an anvil center rod and a head assembly pivotally secured to the anvil center rod about a pivot axis. The head assembly is movable between an operative position and a tilted position. The head assembly includes a housing and cutting member supported within the housing. The housing includes an inner surface defining first and second openings for receiving a suture therethrough. The cutting member includes a knife engageable with the inner surface of the housing between the first and second openings to sever the suture. The inner surface may further include a recess formed between the first and second openings. In embodiments, the recess and the knife may be annular. The cutting member is movable from a first position spaced from the inner surface of the housing to a second position in contact with the inner surface of the housing.

In embodiments, the head assembly may further include a retainer member having an annular body portion and a frangible ring for maintaining the cutting member in the first position. Separation of the frangible ring from the annular body portion may permit movement of the cutting member from the first position to the second position. The anvil assembly may further include a biasing member positioned to urge the head assembly relative to the anvil center rod to position the head assembly in the tilted position.

Also provided is an anvil delivery system. The anvil delivery system includes an anvil assembly and a suture guide assembly. The suture guide assembly includes a guide suture secured to the head assembly and a reel assembly configured for selectively dispensing the guide suture. The guide suture may be received through the first opening in the housing and extend from the second opening in the housing. The reel assembly may include a reel housing and a reel member rotatably received within the reel housing. The guide suture may be supported about the reel member. The reel member may define an annular channel for receiving the guide suture. The reel member may be rotatably supported on the reel housing within an annular cavity in the housing.

In embodiments, the anvil delivery system further includes a tubular guide assembly for trans-oral insertion of the anvil assembly. The tubular guide assembly may include a flexible tube and an adapter configured for operably connecting the flexible tube to the anvil center rod. The tubular guide assembly may further include a retaining suture for retaining the head assembly of the anvil assembly in the tilted position. The retaining suture may be received through third and fourth openings in the housing and is secured between the adapter and the flexible tube.

In addition, a kit for performing a surgical stapling procedure is provided. The kit includes an anvil assembly, a suture guide, and a tubular guide assembly. The suture guide assembly may include a guide suture and a reel assembly. The tubular guide assembly may include a flexible tube and an adapter.

BRIEF DESCRIPTION OF THE DRAWINGS

Various embodiments of the presently disclosed anvil assembly and anvil assembly delivery system are disclosed herein with reference to the drawings wherein:

FIG. 5 is a distal end view of the anvil assembly of FIGS. 1-4;

FIG. 6 is a side cross-sectional view taken along section line 6-6 of FIG. 5;

FIG. 7 is a side cross-sectional view taken along section line 7-7 of FIG. 5;

FIG. 9 is a top view of the anvil assembly of FIGS. 1-7 engaged with an anvil delivery system;

FIG. 10 is an enlarged exploded view of the anvil delivery system of FIG. 9;

FIG. 11 an enlarged top view of the anvil delivery system of FIGS. 9 and 10, engaged with the anvil assembly of FIGS. 1-7;

FIG. 12 is a side cross-sectional view taken along section line 12-12 of FIG. 11;

FIG. 13 is a side cross sectional view of the anvil assembly of FIGS. 1-7, in a pre-fired tilted position, engaged with the anvil delivery system of FIGS. 9-12;

FIG. 14 is an enlarged view of the indicated area of detail shown in FIG. 13;

DETAILED DESCRIPTION OF EMBODIMENTS

Figure 1:
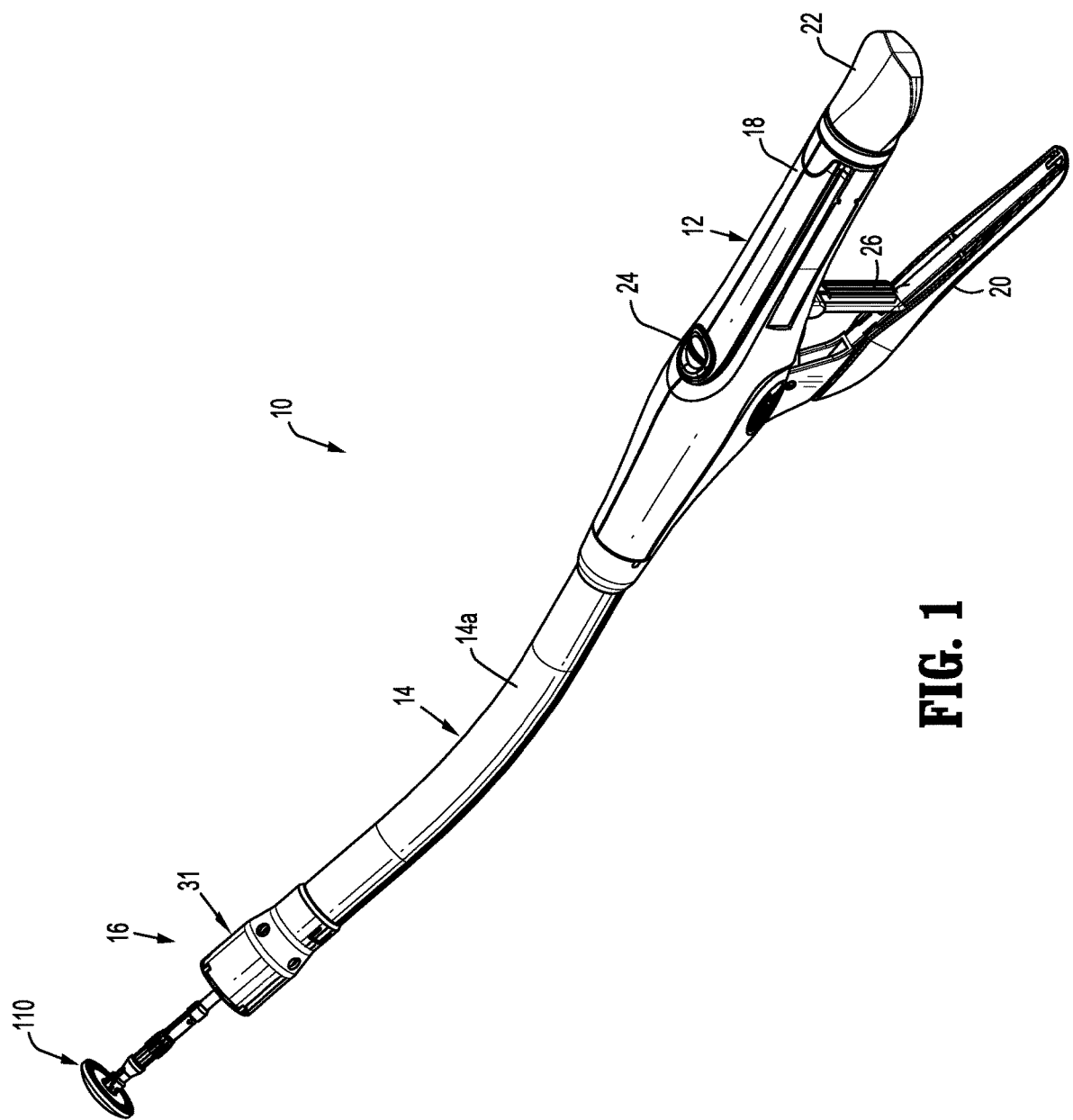
FIG. 1 is a perspective view of a surgical stapling device including an embodiment of an anvil assembly according to the present disclosure.
Figure 2:
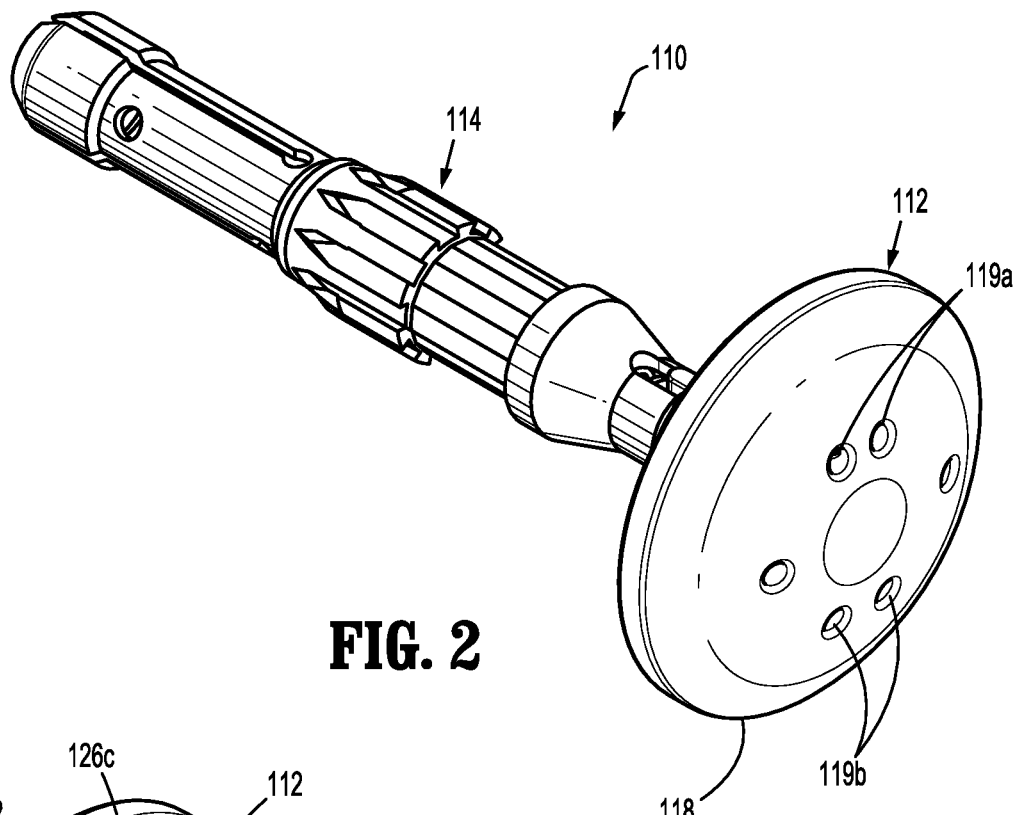
FIG. 2 is a perspective side view of the anvil assembly of FIG. 1 from the distal end.

Embodiments of the presently disclosed anvil assembly delivery system will now be described in detail with reference to the drawings in which like reference numerals designate identical or corresponding elements in each of the several views. Throughout this description, the term "proximal" will refer to the portion of the instrument closest to the operator and the term "distal" will refer to the portion of the instrument furthest from the operator.

FIG. 1 illustrates an embodiment of a surgical stapling device configured for use with tilt anvil assemblies according to the present disclosure. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight, shortened, central body portion. The length, shape and/or the diameter of body portion 14 and distal head portion 16 may also be varied to suit a particular surgical procedure.

With reference still to FIG. 1, handle assembly 12 includes a stationary handle 18, a firing trigger 20, a rotatable approximation knob 22 and an indicator 24. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alpha-numeric labeling, etc., to identify to a surgeon whether the device is approximated and is ready to be fired. Head portion 16 includes an anvil assembly 110 and a shell assembly 31. For a more detailed discussion of surgical stapler 10, please refer to commonly owned U.S. Pat. No. 7,364,060 to Milliman, the contents of which is incorporated herein by reference in its entirety.

Referring now to FIGS. 2-7, an anvil assembly according to an embodiment of the present disclosure is shown generally as anvil assembly 110. Anvil assembly 110 is shown in a non-titled position or operative position. Anvil assembly 110 includes a head assembly 112 and a center rod assembly 114. Head assembly 112 includes a post 116, a housing 118, a backup member or plate 120, a cutting ring 122, a cutting ring cover 123, an anvil plate 124, a spacer or washer 125, a cam latch member 126, and a retainer member 127. Post 116 is monolithically formed with and centrally positioned within housing 118. Alternately, housing 118 and post 116 may be formed separately and fastened together using a known fastening technique, e.g., welding.

As will be discussed in further detail below, housing 118 includes openings 119a, 119b sized and dimensioned to receive one or more sutures "S". During use, a first suture "$S_1$" (FIG. 9) is inserted through openings 119a and is used to retain head assembly 112 in a retracted or first tilted position (FIG. 9) during insertion of anvil assembly 110 within a patient. A second suture "$S_2$" (FIG. 9) is inserted through openings 119b and is configured to permit retrieval of tilt anvil assembly 110 from within a patient. During trans-oral insertion of anvil assembly 110, suture "$S_2$" extends from the mouth of patient, permitting the anvil assembly 110 to be retrieved trans-orally.

With reference still to FIGS. 2-7, anvil plate 124 is supported in an outer annular recess 128 of housing 118 and includes a plurality of staple deforming pockets 130 for receiving and deforming staples. At least one tab 124a extends radially outwardly from anvil plate 124 and is received within a cutout 132 formed in an outer rim of housing 118. Tab 124a and cutout 132 function to align or properly position anvil plate 124 within annular recess 128 of housing 118.

With particular reference to FIGS. 6 and 7, head assembly 112 will be described in detail. Backup plate 120 includes a central opening 134 which is positioned about post 116 within an inner annular recess 136 of housing 118 between post 116 and outer annular recess 128. Backup plate 120 includes a raised platform 120a. Cutting ring 122 includes an opening 122a having a configuration substantially the same as platform 120a. Although platform 120a is illustrated as having a circular shape, other configurations are envisioned, e.g., square, rectangular, triangular, etc. In one embodiment, cutting ring 122 is formed from polyethylene and is fixedly secured to backup plate 120 using, for example, an adhesive, to form a backup plate/cutting ring assembly. Backup plate 120 is formed from a hard material, e.g., a metal. Alternately other materials of construction may be used to construct backup plate 120 and cutting ring 122. Further, backup plate 120 and cutting ring 122, in the alternative, can be formed as a single or unitary structure.

Still referring to FIGS. 6 and 7, a cutting ring cover 123 is secured to an outwardly facing or proximal surface of cutting ring 122 using, for example, an adhesive. In one embodiment, cutting ring cover 123 is formed from a material or materials, which have a hardness greater than that of the cutting ring, e.g., mylar. In one embodiment, cutting ring cover 123 includes two layers of mylar (not shown) which are joined together using an adhesive and a polypropylene coating. Alternately, cutting ring 122 need not have a cover. Cutting ring 122 and backup plate 120 are slidably mounted about post 116. Backup plate 120 includes a pair of inwardly extending fingers 138 which will be described in further detail below.

With reference still to FIGS. 6 and 7, retainer member 127 is positioned in inner annular recess 136 between backup plate 120 and a back wall 118a of housing 118. In one embodiment, retainer member 127 is annular and includes a plurality of deformable tabs 127a which engage a rear surface of backup plate 120. Retainer member 127 prevents backup plate 120 and cutting ring 122 from moving or being pushed into inner annular recess 136 of housing 118 until a predetermined force sufficient to deform tabs 127a has been applied to the backup plate/cutting ring assembly. The predetermined force can be close to but is less than the force applied by an annular cutting blade of a surgical stapling device when it engages, for example, the cutting ring of anvil assembly 110. In one embodiment by way of example, the predetermined force is between about ten pounds and about ninety pounds and can be about thirty (30) pounds. When the predetermined force is reached, e.g., during cutting of tissue, backup plate 120 is urged into inner annular recess 136 and compresses retainer member 127. It is envisioned that other crushable, deformable, collapsible or movement restricting members may be used to retain the backup plate/cutting ring assembly in a fixed position until a predetermined force has been applied to the backup plate/cutting ring assembly.

Turning back to FIG. 4, anvil center rod assembly 114 includes a center rod 152, a plunger 154 and plunger spring 156. A first end of center rod 152 includes a pair of arms 159 which define a cavity 159a. Each arm 159 has a transverse throughbore 158 which is aligned with a central longitudinal axis of center rod 152. Alternately, throughbores 158 can be offset from the longitudinal axis of center rod 152. Post 116 of head assembly 112 is dimensioned to be positioned within cavity 159a and also includes a transverse throughbore (not shown). A pivot member 162 pivotally secures post 116 to center rod 152 via the through bores such that head assembly 112 may be pivotally mounted to anvil center rod assembly 114.

Figure 3:
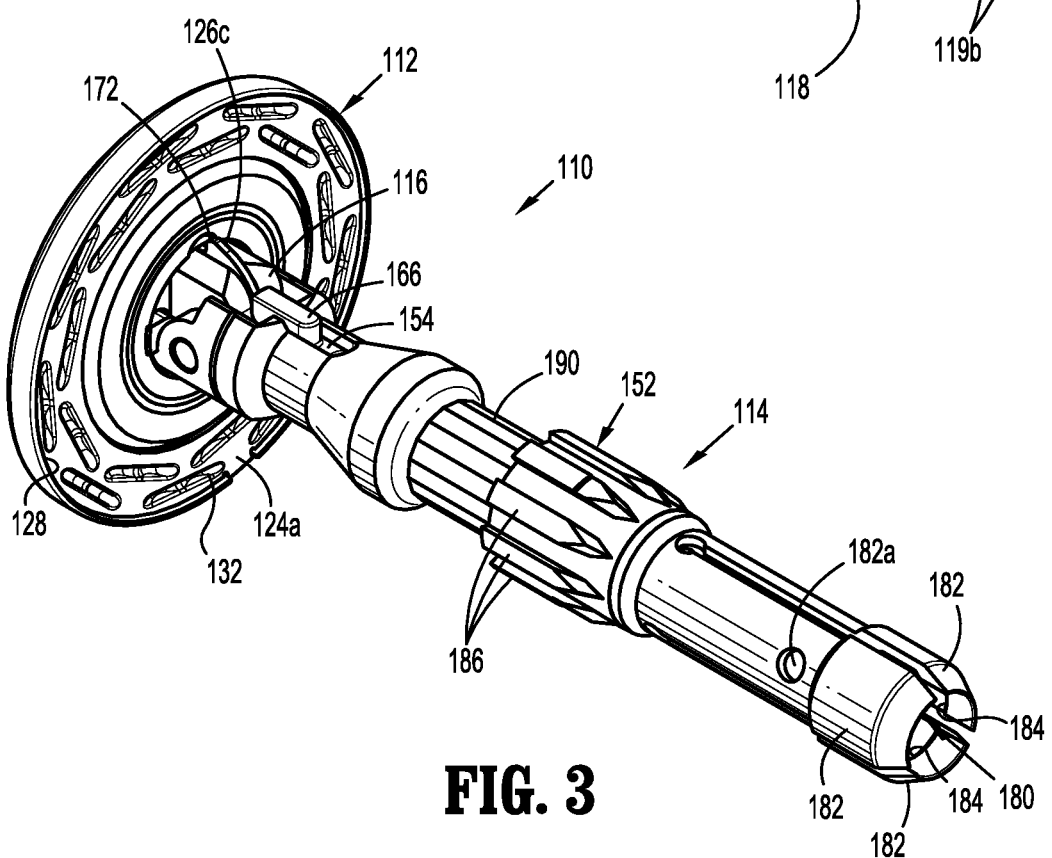
FIG. 3 is a perspective side view of the anvil assembly shown in FIGS. 1 and 2 from the proximal end.
Figure 8:
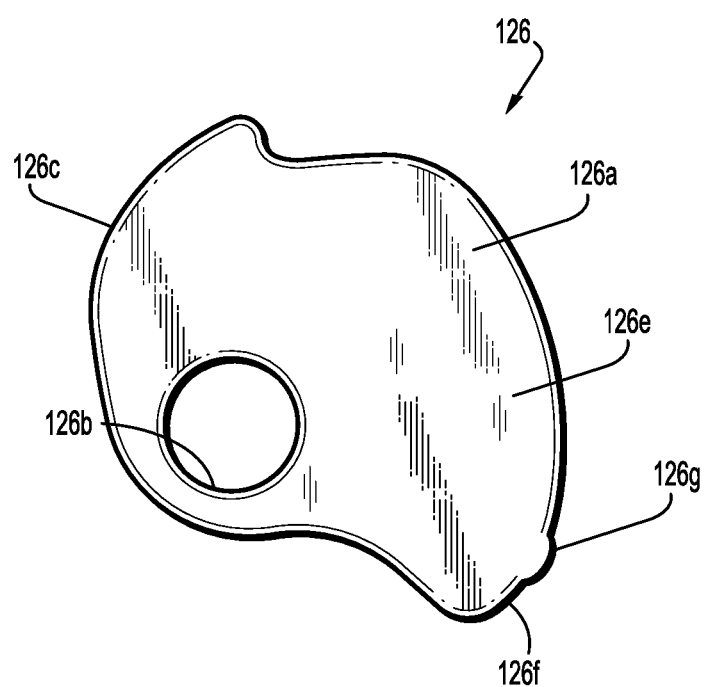
FIG. 8 is an enlarged side view of a cam latch member of the anvil assembly of FIGS. 1-7.

Turning briefly to FIG. 8, cam latch member 126 includes a body 126a having a throughbore 126b. Throughbore 126b is dimensioned to receive pivot member 162 such that cam latch member 126 is pivotally mounted within transverse slot 172 (FIG. 3) of post 116 about pivot member 162. Referring now to FIGS. 3, 6 and 7, cam latch member 126 includes a first body portion 126c which extends partially from slot 172 of post 116 and is positioned to be engaged by a finger 166 of plunger 154. First body portion 126c is configured such that the distance between the surface of first body portion 126c and through bore 126b increase in a clockwise direction about cam latch member 126. In this manner, plunger 154 is able to move forward as cam latch member 126 rotates in a clockwise direction. Additionally, this configuration of first body portion 126c permits plunger 154 to be retracted as cam latch member rotates in a counter-clockwise direction. Cam latch member 126 also includes an edge 126f, including a tab 126 b. A leading portion of edge 126f is configured to be urged into engagement with an inner periphery 120b of backup plate 120 by an engagement finger 166 of plunger 154 when anvil head 112 is in its non-tilted or operative position. Tab 126g is configured to engage backwall 118a of housing 118 to prevent cam latch member 126 from rotating counter-clockwise relative to housing 118.

With reference to FIG. 6, plunger 154 is slidably positioned in a bore 164 formed in the first end of center rod 152. Plunger 154 includes an engagement finger 166 which is offset from the pivot axis of head assembly 112 and biased into engagement with an edge 126c of cam latch 126. Engagement of finger 166 with edge 126c of cam latch 126 presses a leading portion of edge 126f against an inner periphery of back plate 120 to urge head assembly 112 to an operative or non-tilted position on center rod 152.

Turning to FIG. 7, in the pre-fired operative position of head assembly 112, i.e. when head assembly 112 has been pivoted to its non-tilted position, fingers 138 formed on backup plate 120 engage protrusions 152b adjacent top surface 152a of center rod 152 to prevent head assembly 112 from pivoting about pivot member 162. Head assembly 112 may be tilted a degrees (FIG. 13) relative to anvil center rod assembly 114 in the pre-fired tilted position. In one embodiment, head assembly 112 is tilted about seventy degrees (70°) in its pre-fired tilted position; however it should be understood that tilting head assembly 112 to other degrees is also contemplated. Titling of head assembly 112 relative to anvil center rod assembly 114 causes body portion 126c of cam latch member 126 to engage finger 166 of plunger 154. As cam latch assembly 126 rotates with the tilting of head assembly 112, plunger 154 is retracted with bore 164 of anvil center rod assembly 114, thereby compressing spring 156. In this manner, finger 166 of plunger 154 is distally biased against body portion 126c of cam latch member 126.

Figure 4:
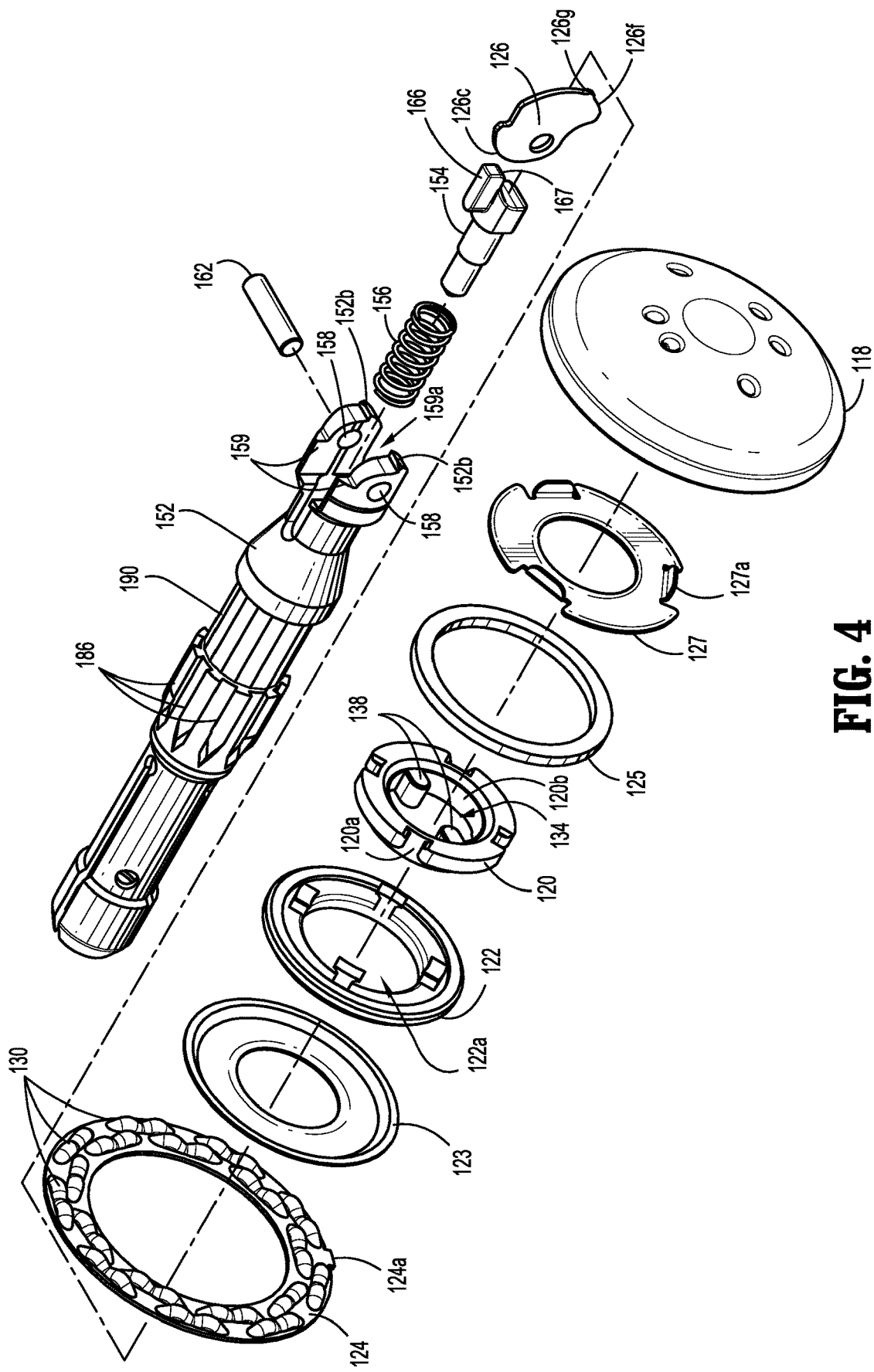
FIG. 4 is an exploded side, perspective view of the anvil assembly of FIGS. 1-3.
Figure 18:
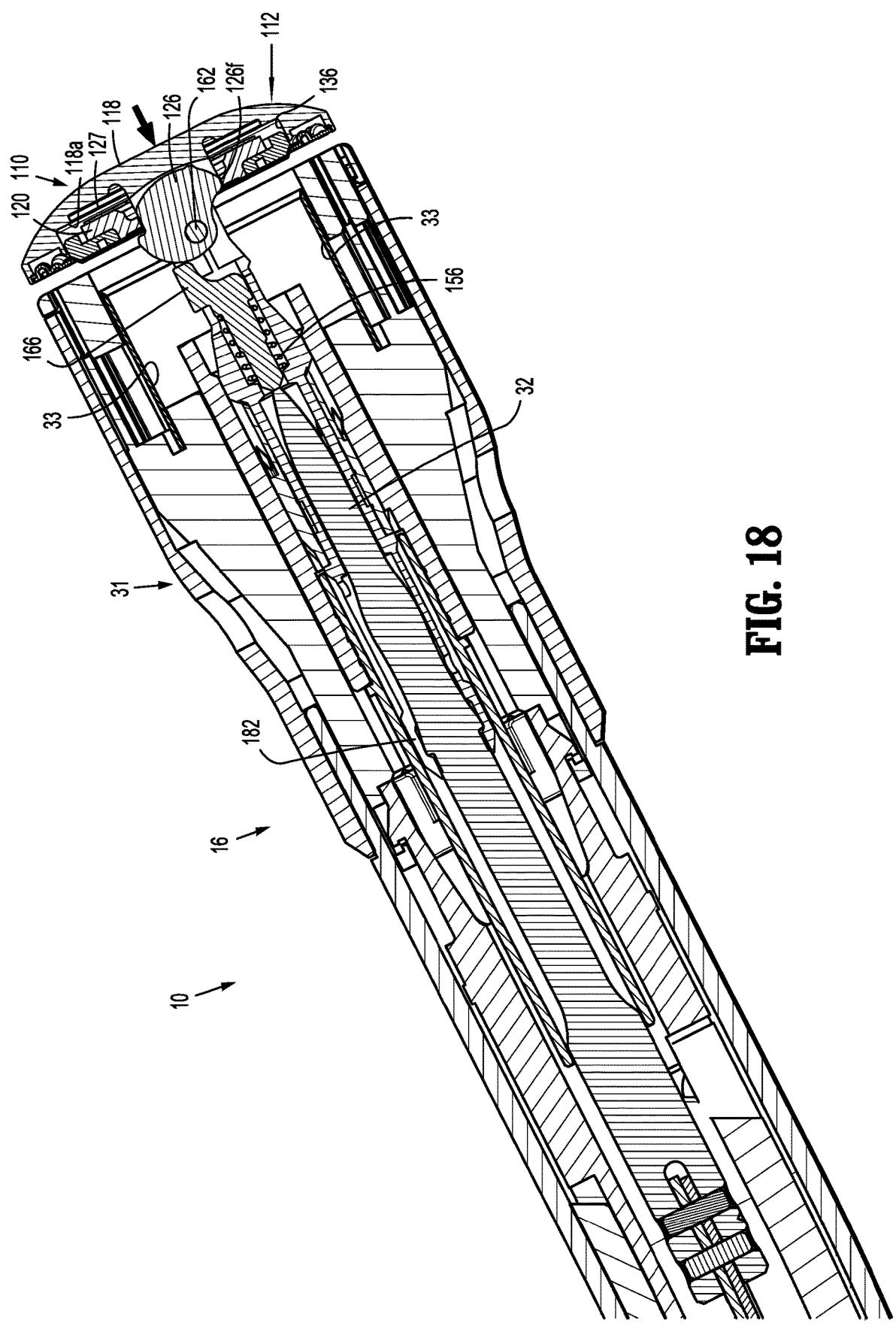
FIG. 18 is an enlarged side cross-sectional view of the distal head portion of the surgical stapling device of FIG. 1 and the anvil assembly of FIGS. 1-7 in a pre-fired non-tilted operative position.
Figure 19:
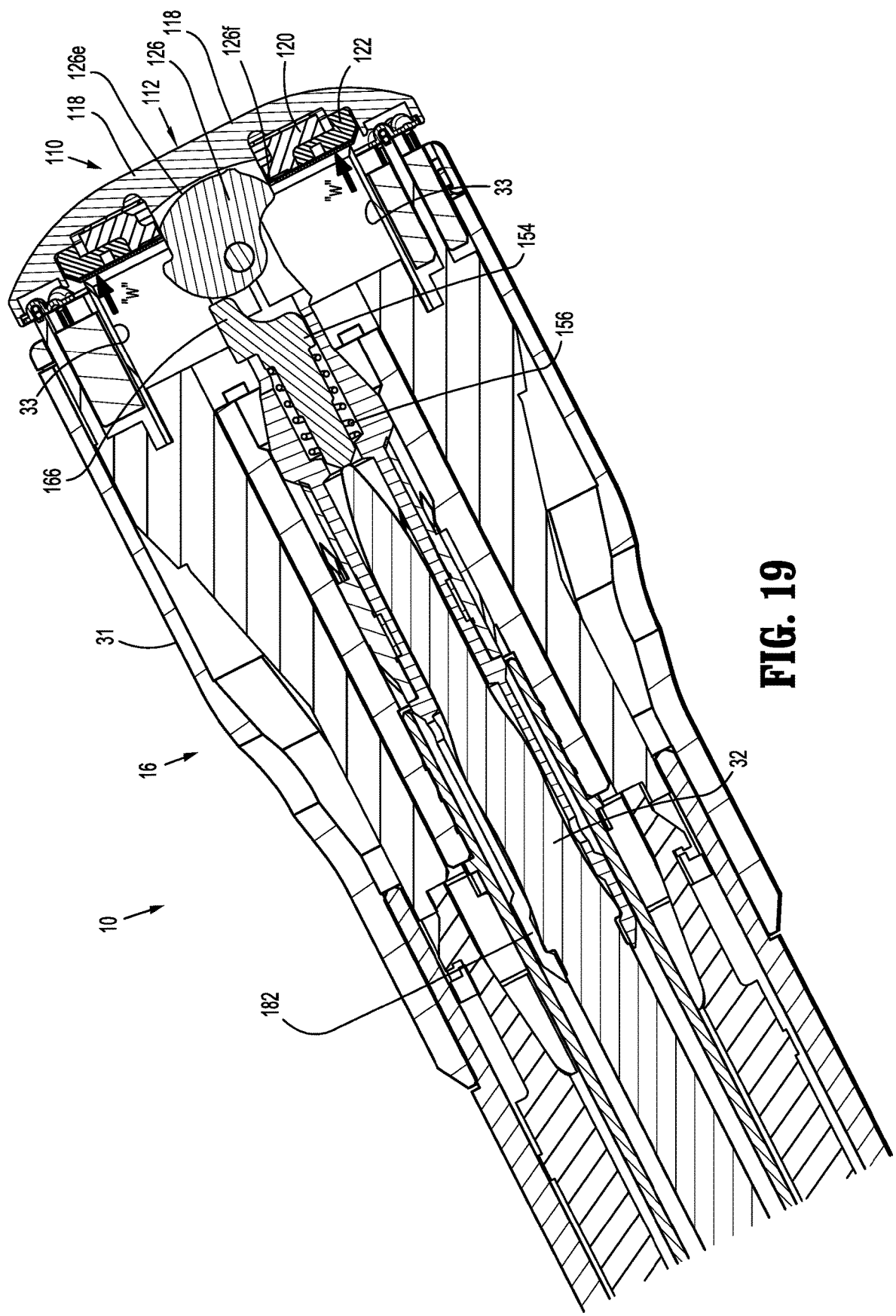
FIG. 19 is an enlarged side cross-sectional view of the distal head portion of the surgical stapling device of FIG. 1 and the anvil assembly of FIGS. 1-7 in a post-fired non-titled operative position.
Figure 20:
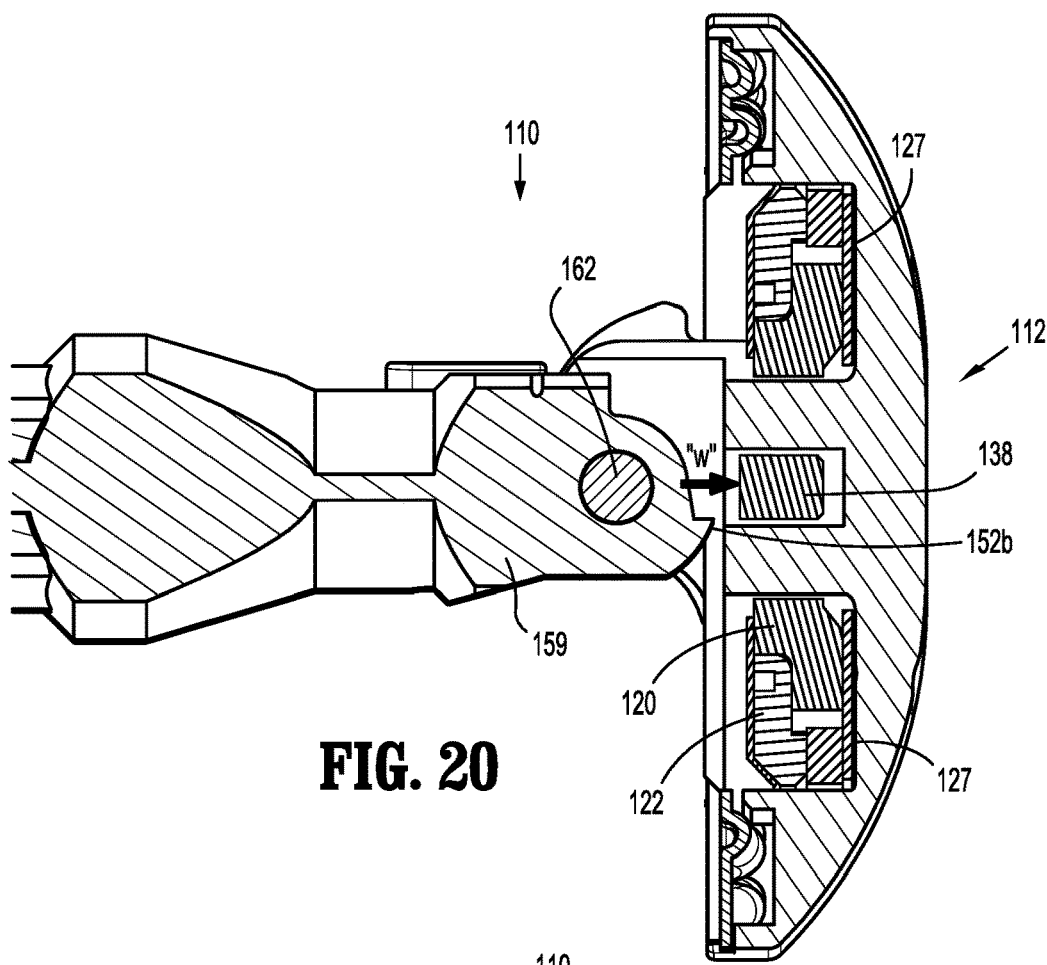
FIG. 20 is an enlarged side cross-sectional view of the distal end of the anvil assembly of FIGS. 1-7 in the post-fired operative position.
Figure 21:
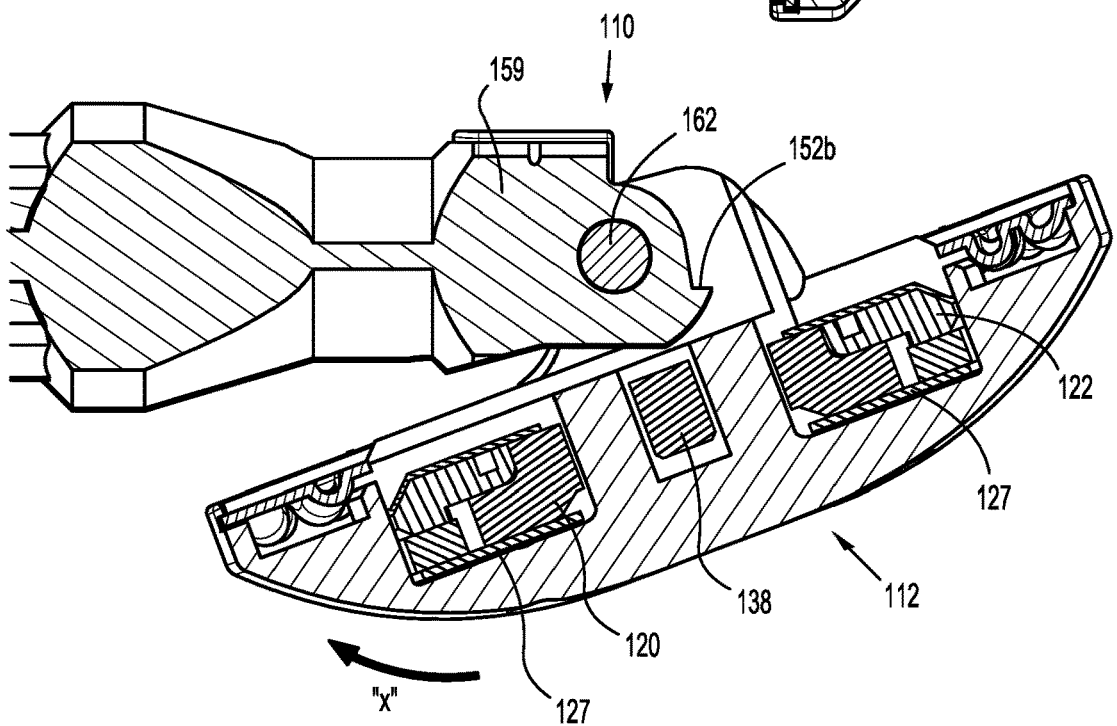
FIG. 21 is an enlarged side cross-sectional view of the distal end of the anvil assembly of FIGS. 1-7 in a post-fired tilted position.

With reference to FIGS. 3 and 4, a second end of center rod 152 includes a bore 180 defined by a plurality of flexible arms 182. Flexible arms 182 each include an opening 182a dimensioned to receive a projection formed on or connected to a shell assembly 31 (FIG. 18). Alternatively, openings 182a may be configured to receive a suture for permitting retrieval of anvil assembly 110. The proximal ends of each of the flexible arms 182 include an internal shoulder 184 dimensioned to releasably engage shell assembly 31 of surgical stapling device 10 to secure anvil assembly 110 to the surgical stapling device. A plurality of splines 186 are formed about center rod 152. Splines 186 function to align anvil assembly 110 with the staple holding portion of a surgical stapling device. Center rod 152 also includes an annular recessed portion 190 to facilitate grasping of anvil assembly 110 by a surgeon with a grasper. Recessed portion 190 may include a roughened or knurled surface or an overmold to facilitate grasping of anvil assembly 110.

With reference now to FIGS. 9-12, a system for delivering anvil assembly 110 within a patient is shown generally as anvil delivery system 50. Anvil delivery system 50 includes a flexible tube 52 and an adapter 62. Flexible tube 52 includes an open end 52a. Adapter 62 and anvil assembly 110 are supported on open end 52a of flexible tube 52. Open end 52a of flexible tube 52 includes a through bore 53 extending therethrough configured to receive a locking pin 54. Open end 52a further includes an opening 55. Closed end 52b of flexible tube 52 is configured for trans-orally receipt in a patient. Flexible tube 52 may include markings or other gradations 56 along the length thereof to indicate to a surgeon how much of flexible tube 52 has been received within the patient during insertion and/or to indicate the length of flexible tube 52 remaining in the patient upon removal.

With particular reference to FIG. 10, adapter 62 includes a first end 62a configured to be received within open end 52a of flexible tube 52 and a second end 62b is configured to be received with in bore 180 formed in center rod 152 of anvil assembly 110. First end 62a includes a series of annular rings 64 configured to frictionally retain first end 62a of adapter 62 within open end 52a of flexible tube 52. Second end 62b of adapter 62 includes a longitudinal guide member 66 configured to be received between flexible arms 182 formed in center rod 152 of anvil assembly 110. In addition, second end 62b of adapter 62 is sized to allow center rod 154 of anvil assembly 110 to freely slide into and off second end 62b of adapter 62. Adapter 62 further includes a first through bore 70 formed in a central hub portion 62c as well as second and third through bores 72, 74 formed in first end 62a. Through bore 72 is configured to align with through bore 53 formed in open end 52a of flexible tube 52 and is sized to receive locking pin 54.

With particular reference now to FIGS. 10, 13 and 14, anvil assembly 110 is supported on anvil delivery system 50. Securing anvil assembly 110 to anvil delivery system 50 requires first that suture "S₁" is thread through openings 119a formed on head assembly 112 such that first and second ends of suture "S₁" are positioned on opposites of center rod 152. Next, second end 62b of adapter 62 is positioned within through bore 180 of center rod 152 such that longitudinal guide 66 is received between two of arm members 182. Each of the first and second ends of suture "S₁" is inserted through opening 55 formed in open end 52a of flexible member 52. Head assembly 112 is then rotated to a first tilted position while first and second ends of suture "S₁" are pulled through opening 55. First end 62a of adapter 62 is then inserted into open end 52a of flexible member. The frictional contact between annular rings 64 of first end 62a of adapter 62 and an inner surface of flexible tube 52 secures adapter 62 to flexible tube 52 and prevents suture "S₁" from loosening. It is envisioned that more than one suture may be used to secure head assembly 112 in a pre-fired tilted position.

Figure 15:
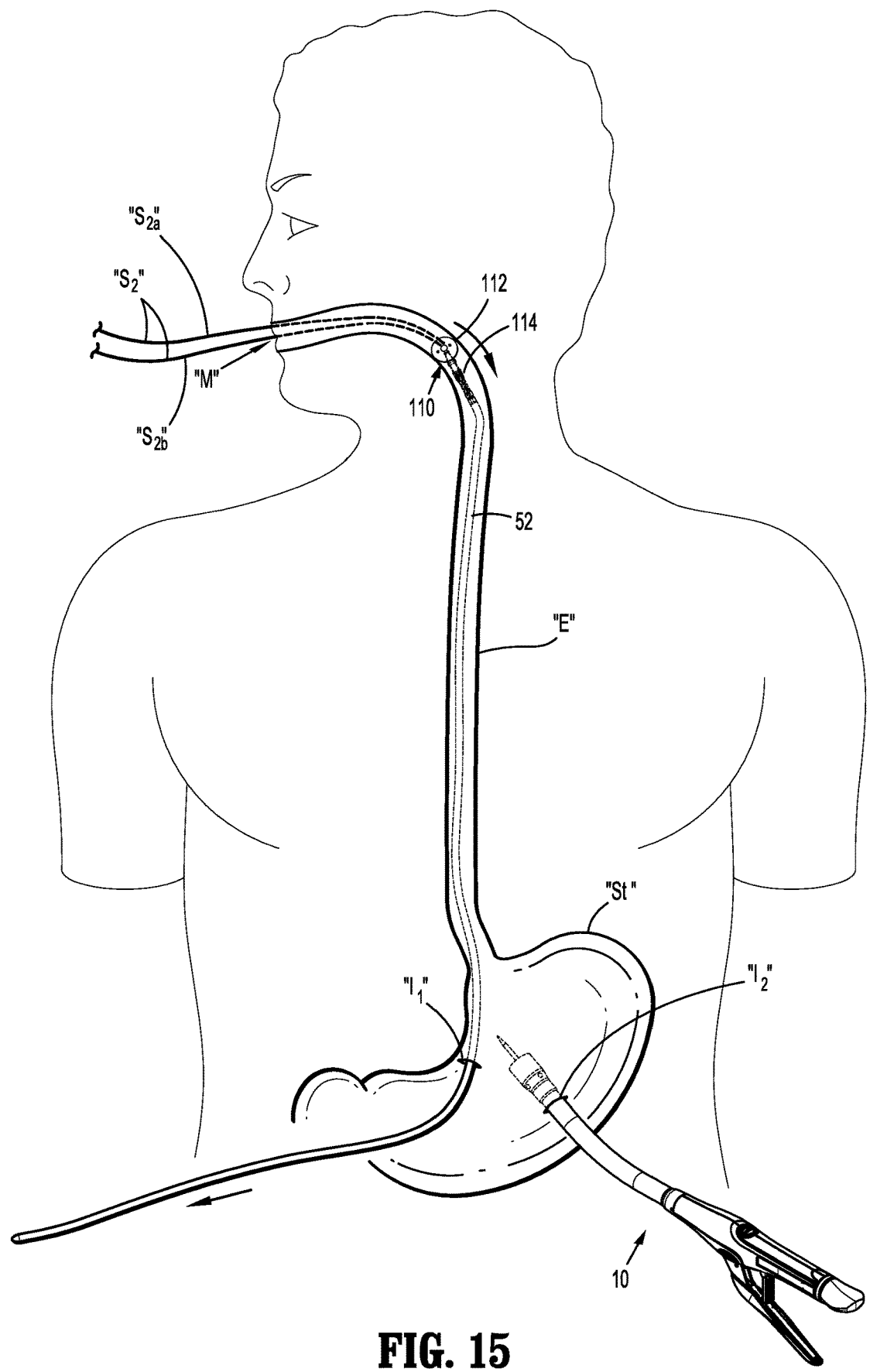
FIG. 15 is an illustration of the anvil assembly and anvil delivery system of FIGS. 11 and 12 being inserted trans-orally into a patient.

With reference now to FIG. 15, a method for delivering anvil assembly 110 to a surgical site within a patient will be described. In one method, anvil assembly 110 is provided in the first tilted position supported on anvil delivery system 50 and ready for delivery. Alternatively, a clinician secures anvil assembly 110 to anvil delivery system 50 as discussed above. Once anvil assembly 110 has been secured to flexible tube 52, the surgeon inserts closed end 52b of flexible tube 52 in the patient's mouth "M" and moves closed end 52b along with flexible tube 52 down through esophagus "E" to a surgical site, i.e., the stomach "St".

After insertion, the surgeon then makes a first incision "I₁" at the surgical site (stomach "St" as shown) to create an inner access to closed end 52b of flexible tube 52 and then pulls open end 52b of flexible tube 52 through first incision "I₁". In some procedures it may be beneficial to pull flexible tube 52 through incision "I₁" until center rod 152 of anvil assembly 110 advances through first incision "I₁". When anvil assembly 110 is properly positioned at the surgical site, the surgeon releases anvil delivery system 50 from anvil assembly 110 by cutting suture "S₁" and separating anvil assembly 110 from second end 62b of adapter 62. Flexible tube 52 (with fitting 62) may then be pulled from the body through first incision "I₁".

Severing of suture "S₁" permits plunger 154 to extend from within bore 164, thereby causing finger 166 to engage body portion 126c of cam latch member 126. Rotation of cam latch member 126 causes edge 126f of latch member 126 to move into engagement with the inner periphery of backup plate 120, thereby urging head assembly 112 to return to a non-tilted operative position. Additionally, the distal end of stapling device 10 may be configured to engage finger 166 of plunger 154 as anvil assembly 110 is attached to surgical stapling device 10. In this manner, the distal end of surgical stapling device 10 urges plunger 154 distally, thereby ensuring the rotation of head assembly 112 to a non-tilted position.

With particular reference to FIG. 15, in one method, a second incision "I₂" is then formed at the surgical site such that distal head portion 16 of surgical stapling device 10 may be received therethrough. Alternatively, distal head portion 16 of surgical stapling device 10 may be received through first incision "I₁" once anvil deliver system 50 has been removed therefrom.

Figure 16:
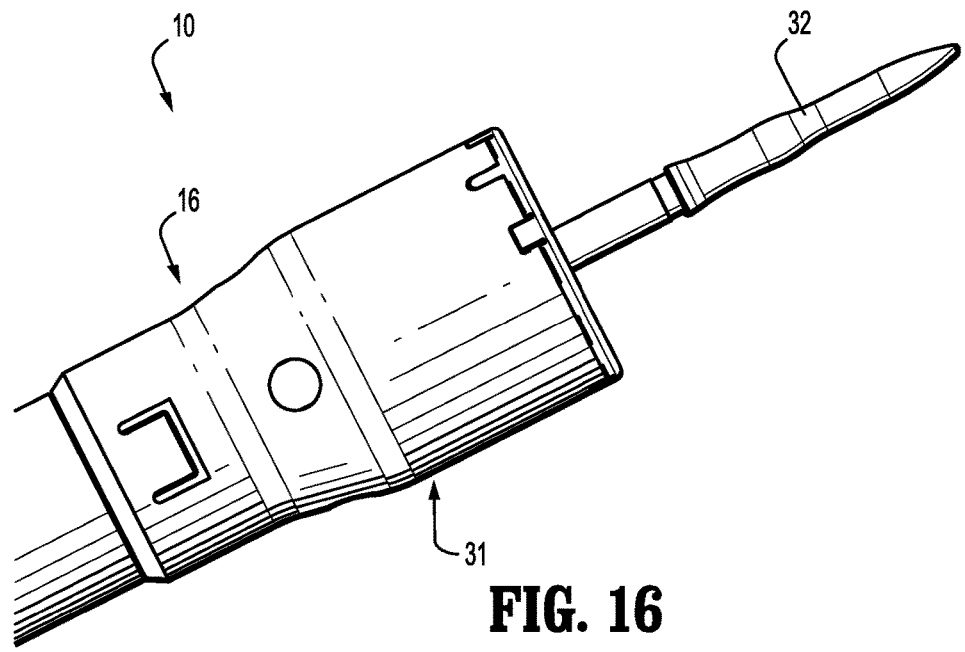
FIG. 16 is an enlarged side view of the distal head portion of the surgical stapling device of FIG. 1 with the anvil assembly removed.
Figure 17:
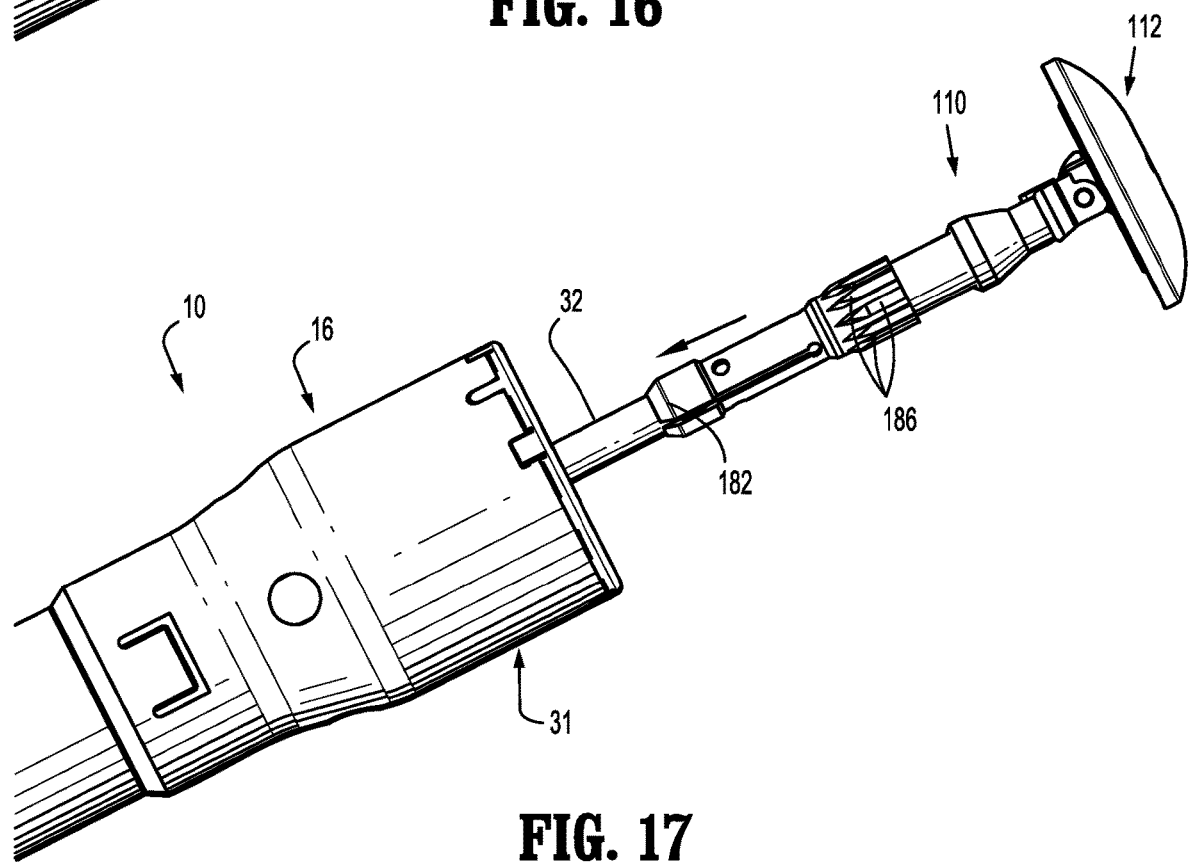
FIG. 17 is an enlarged side view of the distal head portion of the surgical stapling device of FIG. 1 with the anvil assembly of FIGS. 1-7 received thereon.

Turning briefly to FIGS. 16 and 17, anvil assembly 110 is operably received on an anvil retainer 32 extending from shell assembly 31 formed on a distal end of surgical stapling device 10. Once anvil assembly 110 is received on surgical stapling device 10, surgical stapling device 10 operates in the manner discussed in the '060 patent.

The operation of anvil assembly 110 will now be described with reference to FIGS. 18-23. When anvil assembly 110 is in its pre-fired non-tilted position, backup plate 120 is spaced from backwall 118a of housing 118 by retainer 127 and protrusions 152b of center rod 152 engage fingers 138 of backup plate 120 to prevent tilting of head assembly 112 about pivot member 162. Finger 166 of plunger 154 is urged by spring 156 into engagement with body portion 126c of cam latch member 126 to urge cam latch member 126 in a clockwise direction, about pivot member 162 such that edge 126f of cam latch member 126 engages inner periphery 120b of backup member 120.

Figure 22:
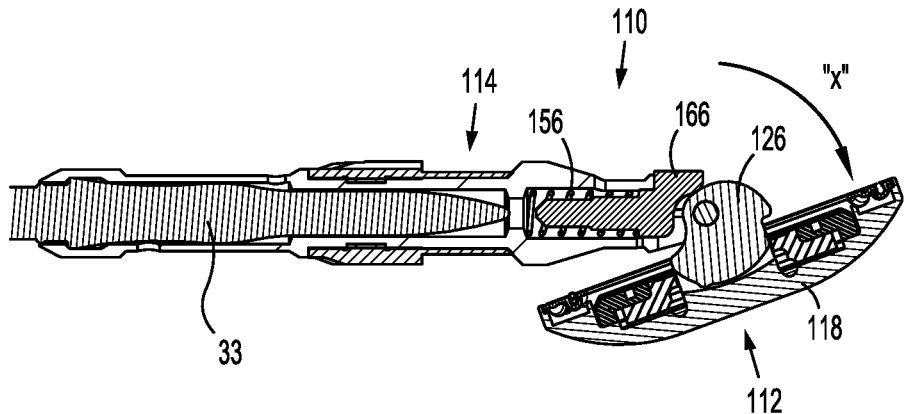
FIG. 22 is a side cross-sectional view of the anvil assembly of FIGS. 1-7 in a post-fired tilted position supported on an anvil retainer of the surgical instrument of FIG. 1.
Figure 22A:
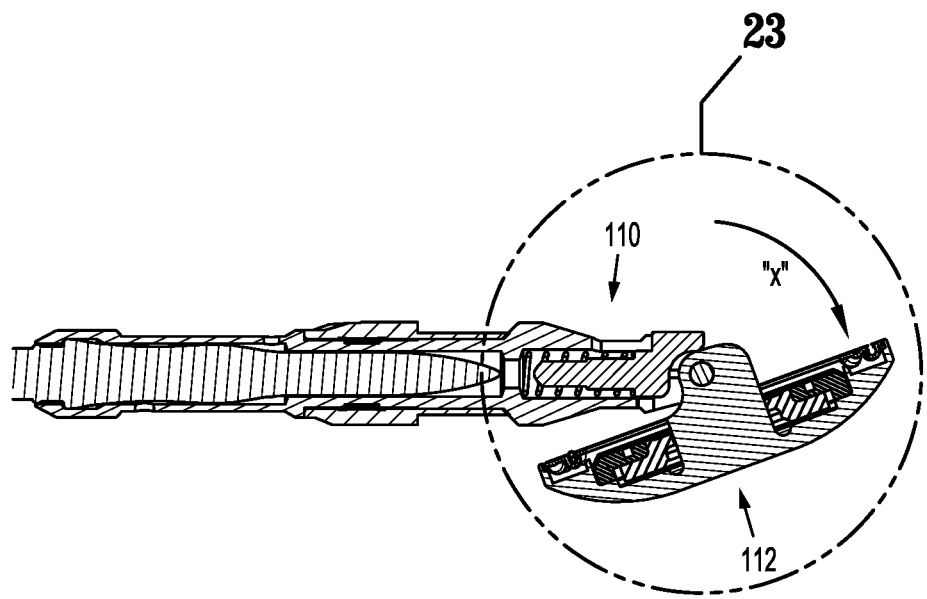
FIG. 22A is another side cross-sectional view of the anvil assembly of FIGS. 1-7 in a post-fired tilted position supported on an anvil retainer of the surgical instrument of FIG. 1
Figure 23:
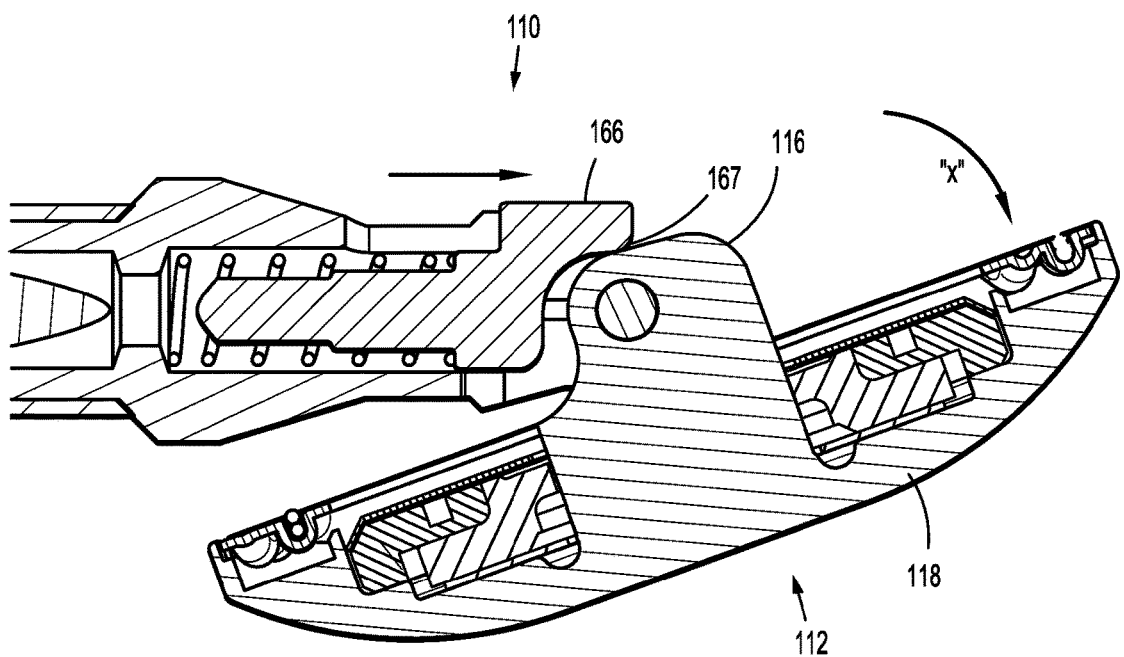
FIG. 23 is an enlarged view of the indicated area of detail shown in FIG. 22A.
Figure 24:
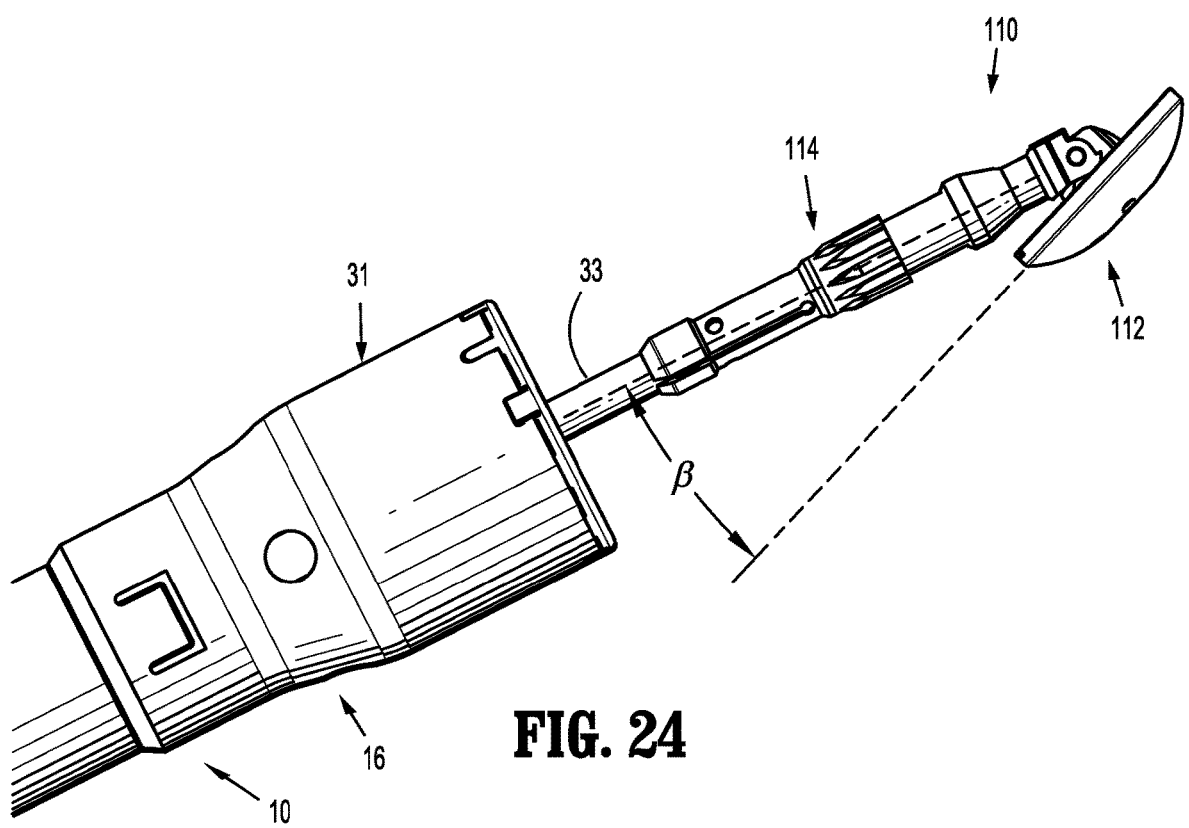
FIG. 24 is a side view of the anvil assembly of FIG. 22 supported on the anvil retainer of the surgical stapling device of FIG. 1 in the post-fired tilted position.

The firing of surgical stapling device 10 causes a knife blade 33 thereof to engage cutting ring 122 to move cutting ring 122 and backup plate 120 into annular recess 136 of housing 118 of head assembly 112. Arrows "W" in FIG. 19 indicate how cutting ring 122 and backup plate 120 move as a result of the firing of surgical stapling device 10. When such movement occurs, deformable tabs 127a of retainer 127 are deformed against backwall 118a of housing 118 and fingers 138 of backup member 120 move away from protrusions 152b of center rod 152. Further, inner periphery 120b of backup plate 120 moves past edge 126f of cam latch member 126 such that cam latch member 126 is urged to pivot about pivot member 162 in the direction indicated by arrow "X" in FIG. 21 by plunger 154 to a position in which body portion 126d is positioned in front of and engages backup plate 120. Engagement of plunger 154 with cam latch member 126 urges head assembly 112 to a second tilted position (FIGS. 22 and 23). It is noted that head assembly 112 will not immediately tilt upon firing of surgical stapling device 10 because, upon firing, head assembly 112 is in an approximated position, i.e., the head assembly 112 is in close alignment with shell assembly 31 of stapling device 10, and, therefore, does not provide room for head assembly 112 to pivot. As such, the head assembly 112 will only begin to tilt when anvil assembly 110 and shell assembly 31 of surgical stapling device 10 are being unapproximated.

As head assembly 112 pivots towards its forward or second tilted position, finger 166 of plunger 154 maintains surface 126e of cam latch member 126 in contact with backup plate 120 to prevent backup plate 120 from sticking to the knife blade as the knife blade is retracted. It is noted that curved surface 126e of cam latch member is configured to eliminate any gap and ensure contact between surface 126e of cam latch member 126 and backup plate 120 to hold backup plate 120 in place during and after the knife blade is retracted such that the cutting ring and backup plate assembly stay in their correct position during continued tilting of anvil assembly 112. Anvil assembly 110 is configured such that head assembly 112 tilts to a forward or second tilted position β degrees (FIG. 23) relative to center rod assembly 114. In one embodiment, head assembly 112 is tilted about seventy degrees (70°) to its second tilted position such that the total pivoting movement of the anvil from the retracted or first tilted position to the forward or second tilted position is about one-hundred and forty degrees (140°). It should, however, be noted that the tilting of head assembly 112 to other degrees is also contemplated.

As described above, the anvil assemblies of the present disclosure are configured to be delivered to a surgical site, e.g., the stomach "St" (FIG. 15), trans-orally. During trans-oral delivery of the anvil assemblies, a retaining suture, i.e., first suture "$S_1$", retains the head assembly of the anvil assembly in a first tilted position and a proximal guide suture, i.e., second suture "$S_2$", includes first and second ends "$S_{2a}$", "$S_{2b}$" that remain external of the patient's mouth "M" that allow the surgeon to dislodge or retrieve the anvil assembly from the patient during trans-oral delivery.

As described above and with reference to FIG. 11, second suture "$S_2$" is threaded through openings 119b in housing 118 of head assembly 112 of anvil assembly 110. Detaching second suture "$S_2$" from anvil assembly 110 requires pulling on first end "$S_{2a}$" of second suture "$S_2$" such that second end "$S_{2b}$" of second suture "$S_2$" travels from external the patient's mouth "M" (FIG. 15), where it is accessible by the surgeon, through the patient's mouth "M" and upper gastrointestinal (GI) tract, e.g., esophagus "E" and stomach "St" (FIG. 15) and through the openings 119b in housing 118 of head assembly 112 of anvil assembly 110 before having to travel back through the upper GI tract and out the patient's mouth "M".

With reference now to FIGS. 25-33, an anvil assembly according to alternate embodiment of the present disclosure is shown generally as anvil assembly 210. As will be described in further detail below, anvil assembly 210 is configured such that second suture "$S_2$" (FIG. 25) is severed during a stapling procedure to detach second suture "$S_2$" from anvil assembly 210 and to permit withdrawal of the second suture "$S_2$" from the patient by pulling on first and second ends "$S_{2a}$", "$S_{2b}$" of the second suture "$S_2$". In this manner, the second suture "$S_2$" is separated from the anvil assembly 210 and withdrawn from the patient without having to pull the second end "$S_{2b}$" of the second suture "$S_2$" through the body lumen (FIG. 15) of the patient, i.e., the mouth "M", the esophagus "E", and the stomach "St".

Figure 25:
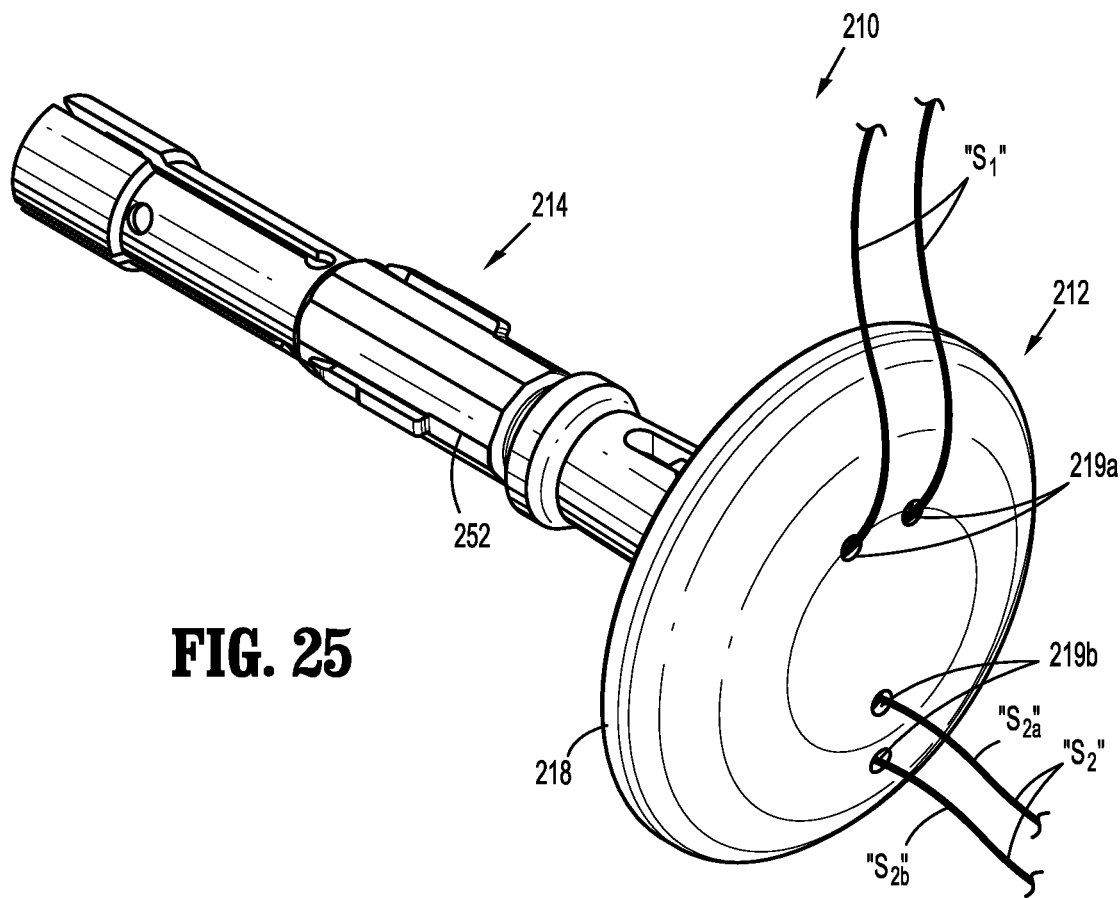
FIG. 25 is a side perspective view of an anvil assembly according to another embodiment of the present disclosure in the operative position.
Figure 26:
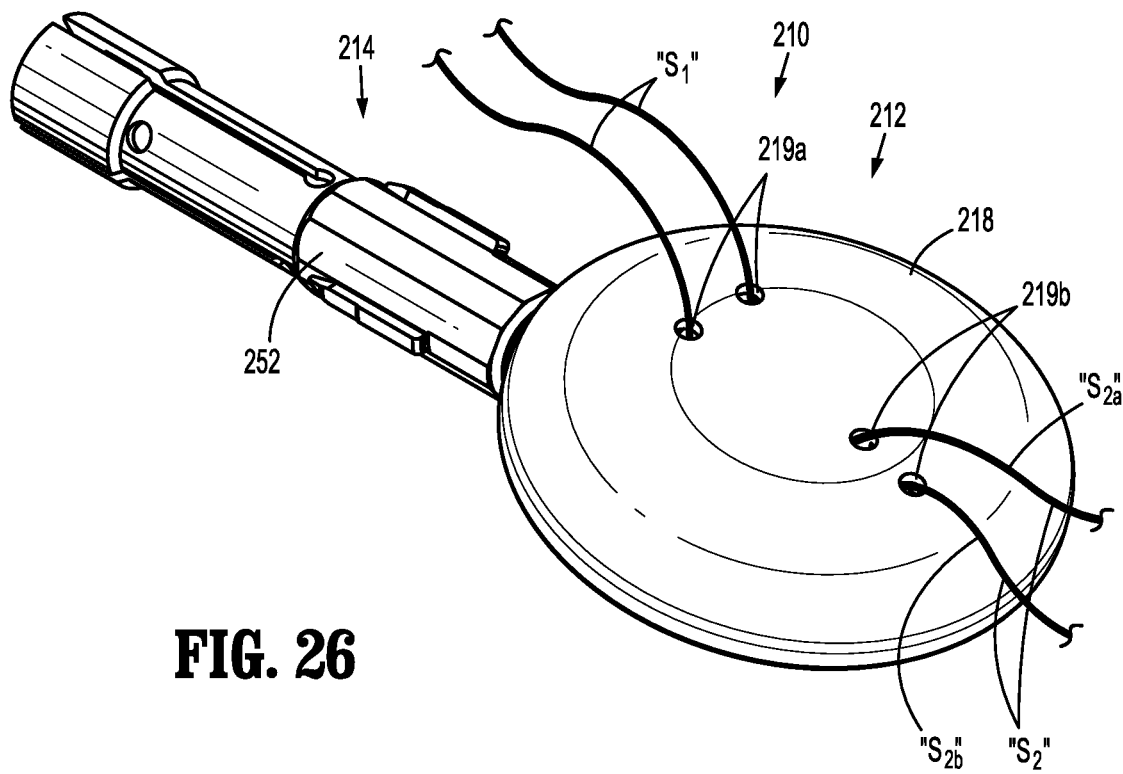
FIG. 26 is a side perspective view of the anvil assembly of FIG. 25 in the first tilted position.
Figure 27:
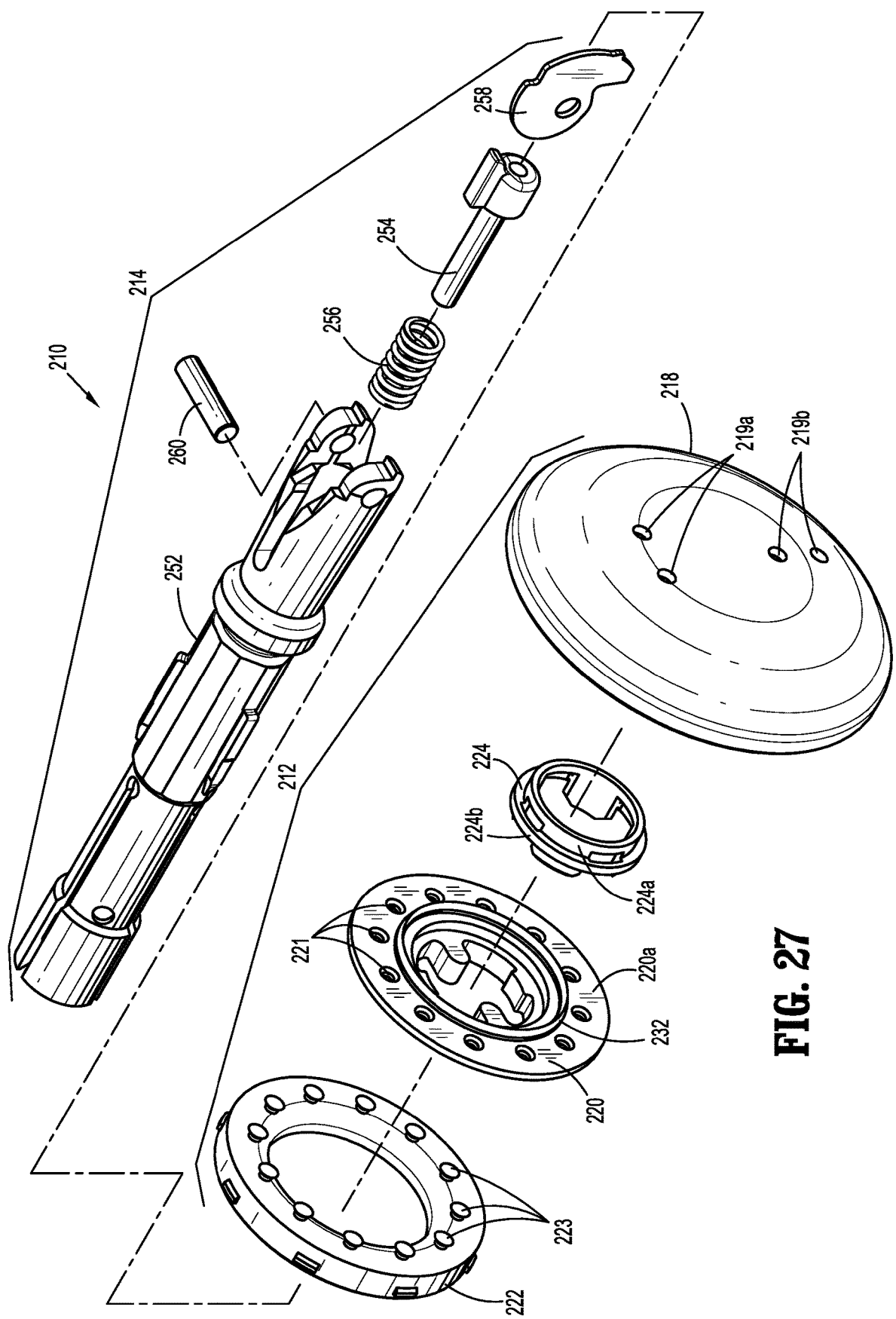
FIG. 27 is an exploded perspective view of the anvil assembly of FIG. 25.

With reference to FIGS. 25-27, the anvil assembly 210 is substantially similar to the anvil assembly 110 described hereinabove and will only be described in detail as relates to differences between the anvil assembly 210 and the anvil assembly 110. The anvil assembly 210 includes a head assembly 212 and a center rod assembly 214. The head assembly 212 is pivotable relative to the center rod assembly 214 and includes a housing 218, a backup member 220, a cutting ring 222, and a retainer member 224. An anvil plate 226 (FIG. 28) is supported on an outer rim 230b (FIG. 28) of the housing 218 and includes a plurality of staple deforming pockets 226a (FIG. 28) for receiving and deforming staples (not shown). The center rod assembly 214 includes a center rod 252, a plunger 254 for engaging the head assembly 212, a plunger spring 256 for biasing the plunger 254 in a distal direction, a cam latch member 258 received within the head assembly 212, and a pivot pin 260 pivotally connecting the head assembly 212 to the center rod 252.

Figure 28:
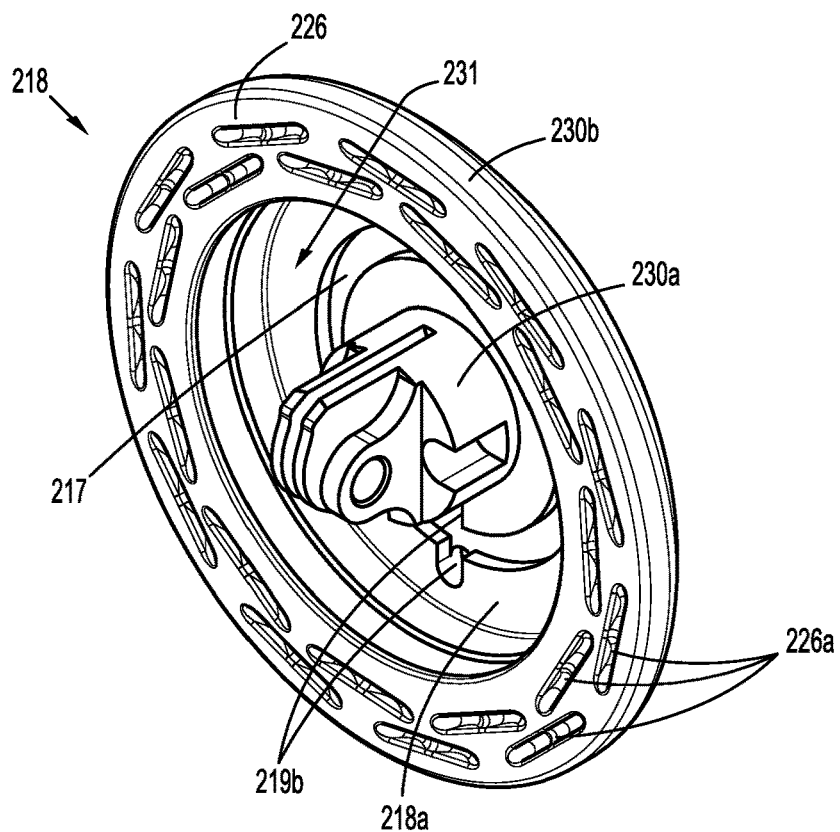
FIG. 28 is a bottom perspective view of a housing of the anvil assembly of FIG. 25.
Figure 28A:
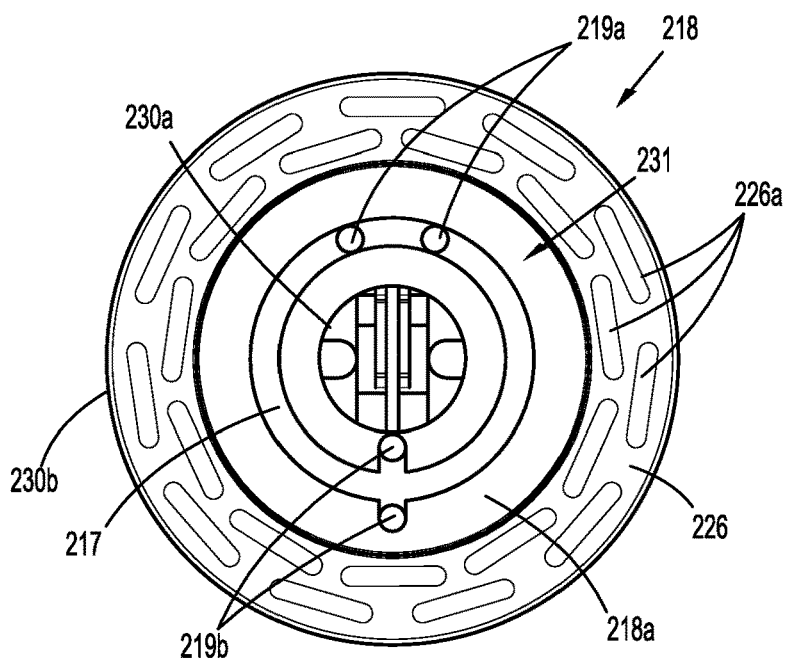
FIG. 28A is an end view of the housing of the anvil assembly of FIG. 25 from a proximal end.
Figure 29:
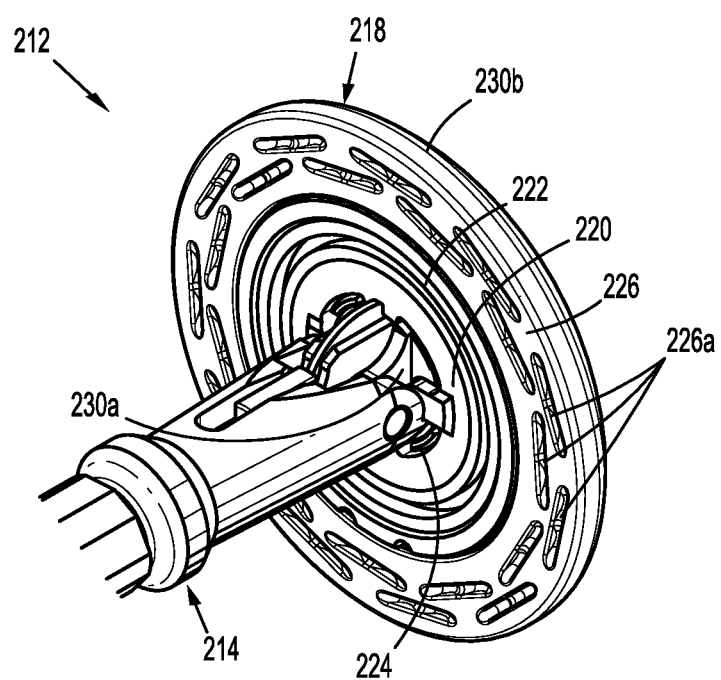
FIG. 29 is a bottom perspective view of a head assembly of the anvil assembly of FIG. 25.
Figure 30:
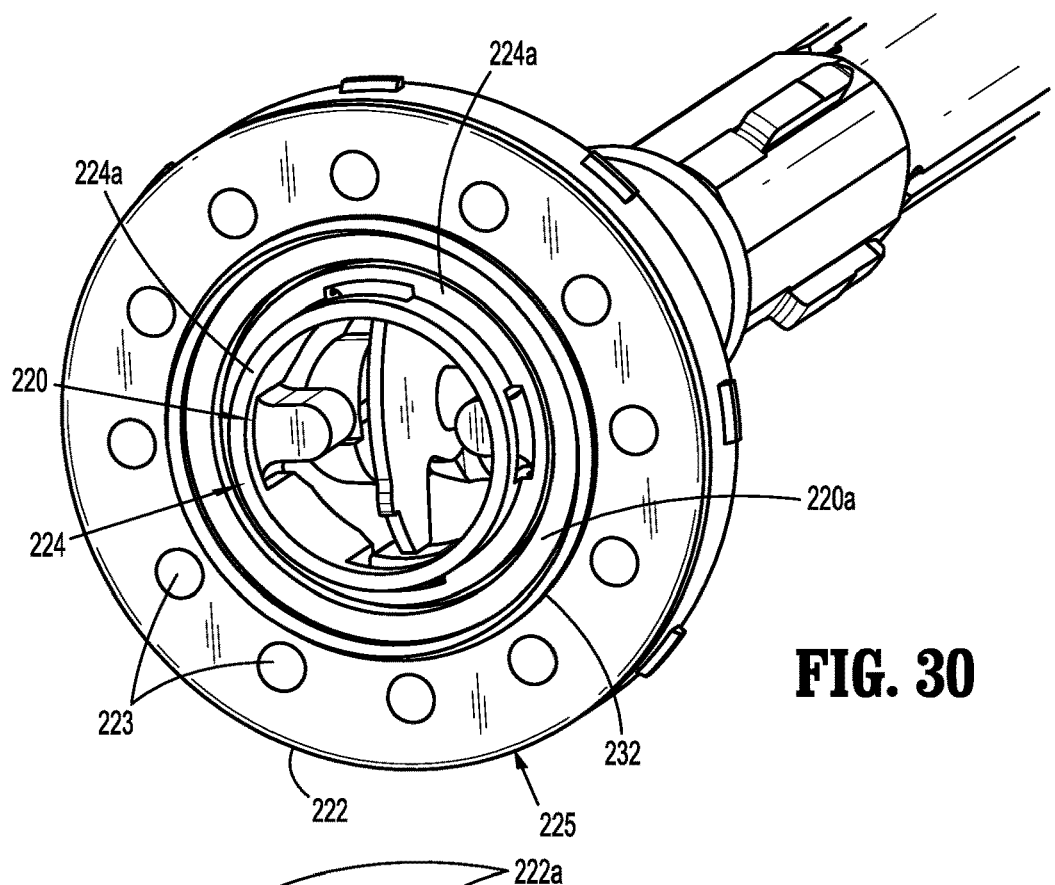
FIG. 30 is a top perspective view of the anvil assembly of FIG. 25 with the housing of FIG. 28 removed.
Figure 31:
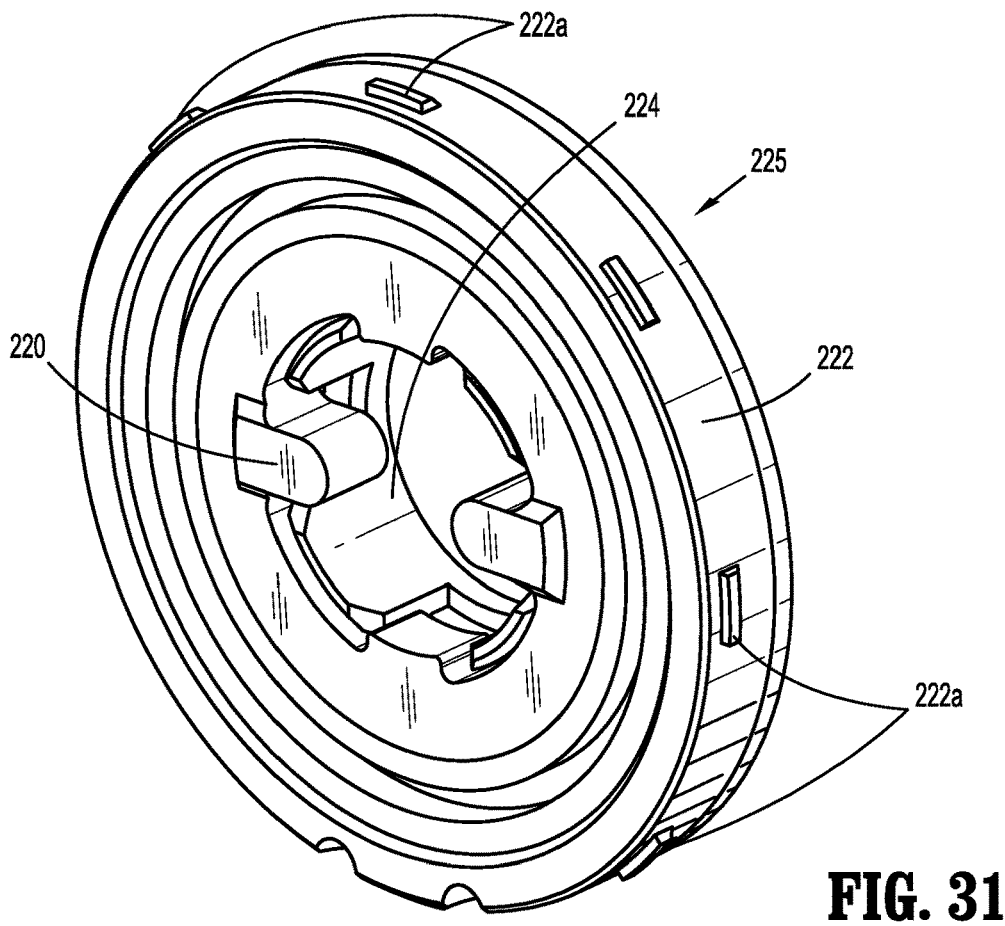
FIG. 31 is a bottom perspective view of a backup member/cutting ring assembly of the anvil assembly of FIG. 25.

Referring to FIGS. 27, 28, and 28A, the housing 218 of the head assembly 212 of the anvil assembly 210 includes a center post 230a and defines a cavity 231 between the center post 230a and the outer rim 230b. An inner surface 218a of the housing 218 defines a recess 217 spaced outward from and formed about the center post 230a within the cavity 231. A first and second pair of openings 219a, 219b (FIG. 25) extend through the inner surface 218a of the housing 218. The first pair of openings 219a receives the first suture "$S_1$" and the second pair of openings 219b receives the second suture "$S_2$". More particularly, the second pair of openings 219b extends through the inner surface 218a of housing 218 on either side of the recess 217 such that when the second suture "$S_2$" (FIG. 32) is received through the second pair of opening 219b, the second suture "$S_2$" extends across the recess 217. Although the recess 217 is shown as being annular and extending completely about the center post 230a of housing 218, it is envisioned that recess 217 need only extend a distance to facilitate passage of the second suture "$S_2$" and, thus, may extend only partially about the center post 230a. In alternative embodiments, housing 218 is formed without a recess 217 and the second suture "$S_2$" is received through the second pair of openings 219b and extends directly across the inner surface 218a of housing 218.

With reference to FIG. 27-31, the backup member 220, the cutting ring 222, and the retainer member 224 are received within the cavity 231 (FIG. 28A) of the housing 218 about the center post 230a of housing 218. The backup member 220 is secured to the cutting ring 222 to form a backup member/cutting ring assembly 225. As shown, the backup member/cutting ring assembly 225 is formed by overmolding the backup member 220 to the cutting ring 222. In particular, during the overmolding of the backup member 220 to the cutting ring 222, a plurality of post 223 are formed that extend through openings 221 of the cutting ring 222 to secure the backup member 220 to the cutting ring 222. Alternatively, the backup member/cutting ring assembly 225 is formed as a single component or as two components that are secured together using mechanical fasteners or in any other suitable manner. The backup member/cutting ring assembly 225 is movable within the cavity 231 from a proximal position (FIG. 32) to a distal position (FIG. 33). The backup member/cutting ring assembly 225 is retained in the proximal position (FIG. 32) within the cavity 231 of the housing 218 by the retainer member 224.

The retainer member 224 includes an annular body portion 224a and a frangible ring 224b supported on the annular body portion 224a. The frangible ring 224b maintains the backup member/cutting ring assembly 225 in the proximal position until a predetermined force sufficient to fracture or separate the frangible ring 224b from the annular body portion 224a of the retainer member 224 is applied to the backup member/cutting ring assembly 225 by an annular knife 33 (FIG. 19) of surgical stapling device 10 (FIG. 1). The backup member/cutting ring assembly 225 is maintained within the cavity 231 of housing 218 by a plurality of tabs 222 (FIG. 31) extending outwardly from cutting ring 222 and engaging the outer rim 230b of the housing 218.

For a detailed description of the structure and function of an exemplary backup member/cutting ring assembly 225 and an exemplary retainer member 224, please refer to commonly owned U.S. application Ser. No. 14/078,766, the content of which is incorporated herein by reference in its entirety.

The backup member/cutting ring assembly 225 includes a knife 232 that extends from a distal surface 220a of the backup member 220 and is aligned with the recess 217 defined within the housing 218. When the backup member 220 is secured to cutting ring 222 to form the backup member/cutting ring assembly 225, the knife 232 extends distally beyond the distal surface 220a (FIG. 30) of the backup member 220 towards the recess 217. Although shown has having an annular configuration and extending from the backup member 220, it is envisioned that the knife 232 may include any configuration suitable for receipt within recess 217 formed in inner surface 218a (FIG. 28) of housing 218. For example, in embodiments, the length of the knife 232 corresponds to the length of the recess 217 and, thus, as discussed above with regard to recess 217, need only be of a length to facilitate cutting of the second suture "$S_2$". In embodiments of housing 218 without the recess 217, knife 232 is configured to engage the inner surface 218a of housing 218.

Figure 32:
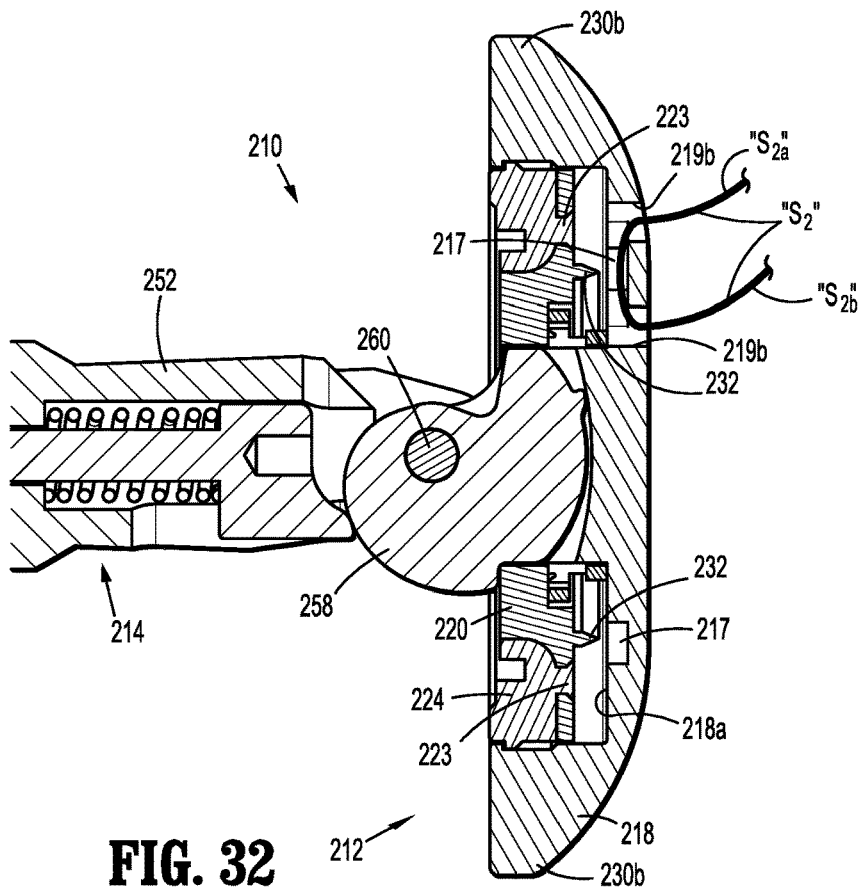
FIG. 32 is a side cross-sectional view of the anvil assembly of FIG. 25 in the operative position with the backup member/cutting ring assembly in a first or proximal position.
Figure 33:
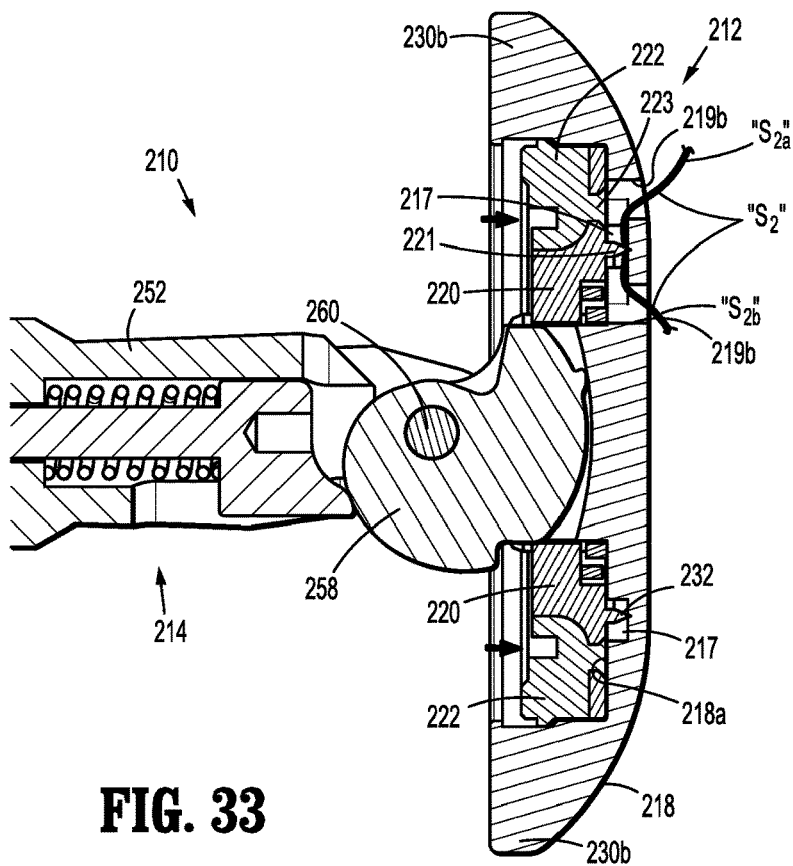
FIG. 33 is a side cross-sectional view of the anvil assembly of FIG. 25 in the operative position with the backup member/cutting ring assembly in a second or distal position.

With particular reference now to FIG. 32, when the head assembly 212 of the anvil assembly 210 is in a pre-fired condition, the backup member/cutting ring assembly 225 and thus, the knife 232 extending from the backup member 220, are longitudinally spaced from the inner surface 218a of the housing 218. As noted above, the backup member/cutting ring assembly 225 is maintained in the proximal position through engagement with the frangible ring 224b of retainer member 224 and is retained within the cavity 231 of the housing 218 through engagement of the plurality of tabs 222a of the cutting ring 222 with the outer rim 230b of the housing 218.

As discussed above with respect to FIG. 19, during firing of the surgical stapling device 10, an annular knife 33 is advanced distally from shell assembly 31, as indicated by arrow "w". With reference now to FIG. 32, when the anvil assembly 210 is attached to the shell assembly 31 (FIG. 19) of surgical stapling device 10 (FIG. 19), distal movement of the annular knife 33 (FIG. 19) causes the knife 33 to engage the cutting ring 222 of the backup member/cutting ring assembly 225 of the head assembly 212. When the predetermined force required to separate or fracture the frangible ring 224b of the retainer member 224 from the annular body portion 224a of the retainer member 224 is applied to the frangible ring 224b by the knife 33, the backup member/cutting ring assembly 225 is moved distally within the cavity 231 of the housing 218 about the center post 230a. Continued force from the knife 33 causes the backup member/cutting ring assembly 225 to move distally until the backup member/cutting ring assembly 225 engages the inner surface 218a of the housing 218. As the backup member/cutting ring assembly 225 is moved distally, the knife 232 of the backup member 220 is received within the recess 217 formed in the inner surface 218a of the housing 218 causing the knife 232 to engage and sever second suture "$S_2$".

Once the second suture "$S_2$" is severed, each half of the severed second suture "$S_2$" is independently removed transorally from the patient by pulling on the first and second ends "$S_{2a}$", "$S_{2b}$" of the second suture "$S_2$". By severing the second suture "$S_2$" in this manner, the surgeon is able to disengage the second suture "$S_2$" from the anvil assembly 210 and directly remove each half of the second suture "$S_2$" from within the patient without having to pull the second end "$S_{2b}$" of second suture "$S_2$" through the openings 219b in the anvil assembly 210 and back out of a patient through the body lumen. If the second suture "$S_2$" were to be removed from the patient without severing the suture into two halves, one end "$S_{2a}$", "$S_{2b}$" of the second suture "$S_2$" would have to be pulled into the body lumen of the patient and through the anvil assembly 210 before being pulled back through the body lumen.

As noted above, the second suture "$S_2$" facilitates placement of the anvil assembly 210 within the stomach "St" (FIG. 15) of the patient. The second suture "$S_2$" may be used to dislodge the anvil assembly 210 if it becomes stuck within a body lumen during trans-oral delivery and/or to retrieve the anvil assembly 210 in the event of an emergency. Since the second suture "$S_2$" remains attached to the anvil assembly 210 throughout the placement and attachment of the anvil assembly 210 to the surgical stapling device 10 (FIG. 1), and until the stapling procedure is completed, the second suture "$S_2$" may be used to dislodge and/or retrieve the anvil assembly 210 at any point up to the second suture "$S_2$" being severed.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil delivery system comprising:
   an anvil assembly including,
      an anvil center rod; and
      a head assembly pivotally secured to the anvil center rod about a pivot axis between a first position and a second position, the head assembly including a housing and a cutting member supported within the housing, the cutting member including a knife;
   a first suture engaged with the housing to secure the head assembly in the first position; and
   a second suture engaged with the housing to facilitate retrieval of the anvil assembly, wherein the knife is engageable with the second suture to sever the second suture.

2. The anvil delivery system of claim 1, wherein the housing defines first and second openings that receive the second suture.

3. The anvil delivery system of claim 2, wherein the housing includes an inner surface defining a recess between the first and second openings.

4. The anvil delivery system of claim 3, wherein the cutting member is movable from a first position spaced from the inner surface of the housing to a second position in contact with the inner surface of the housing.

5. The anvil delivery system of claim 1, further including a suture guide assembly releasably supporting the second suture.

6. The anvil delivery system of claim 5, further including a tubular guide assembly for trans-oral insertion of the anvil assembly.

7. The anvil delivery system of claim 6, wherein the tubular guide assembly includes a flexible tube and an adapter operably connecting the flexible tube to the anvil center rod.

8. The anvil delivery system of claim 7, wherein the housing includes third and fourth openings, the first suture received through the third and fourth openings in the housing and secured between the adapter and the flexible tube.

9. An anvil delivery system comprising:
an anvil assembly including,
an anvil center rod; and
a head assembly pivotally secured to the anvil center rod about a pivot axis, the head assembly including a housing and cutting member supported within the housing, the cutting member includes a knife and is movable from a first position to a second position; and
a suture engaged with the housing to facilitate retrieval of the anvil assembly, wherein the knife is engageable with the suture to sever the suture.

10. The anvil delivery system of claim 9, wherein the housing defines first and second openings that receive the second suture.

11. The anvil delivery system of claim 10, wherein the housing includes an inner surface defining a recess between the first and second openings.

12. The anvil delivery system of claim 9, wherein the cutting member is movable from a first position spaced from the inner surface of the housing to a second position in contact with the inner surface of the housing.

13. The anvil delivery system of claim 9, wherein the head assembly further includes a retainer member having an annular body portion and a frangible ring for maintaining the cutting member in the first position, wherein separation of the frangible ring from the annular body portion permits movement of the cutting member from the first position to the second position.

14. The anvil delivery system of claim 9, further including a biasing member positioned to urge the head assembly relative to the anvil center rod to position the head assembly in the tilted position.

15. The anvil delivery system of claim 9, further including a suture guide assembly releasably supporting the suture.

16. The anvil delivery system of claim 15, further including a tubular guide assembly for trans-oral insertion of the anvil assembly.

17. The anvil delivery system of claim 16, wherein the tubular guide assembly includes a flexible tube and an adapter operably connecting the flexible tube to the anvil center rod.

18. The anvil delivery system of claim 16, wherein the tubular guide assembly further includes a retaining suture for retaining the head assembly of the anvil assembly in the tilted position.

19. The anvil delivery system of claim 18, wherein the retaining suture is received through third and fourth openings in the housing and is secured between the adapter and the flexible tube.

* * * * *